US009433628B2

(12) United States Patent
Ajani et al.

(10) Patent No.: US 9,433,628 B2
(45) Date of Patent: Sep. 6, 2016

(54) ENZYMATIC PROCESS FOR OBTAINING 17α-MONOESTERS OF CORTEXOLONE AND/OR ITS 9,11-DEHYDRODERIVATIVES

(71) Applicant: Cassiopea S.P.A., Lainate, Milan (IT)

(72) Inventors: Mauro Ajani, Lainate (IT); Luigi Moro, Cairate (IT)

(73) Assignee: Cassiopea SPA, Lainate (IT)

( * ) Notice: Subject to any disclaimer, the term of this patent is extended or adjusted under 35 U.S.C. 154(b) by 219 days.

(21) Appl. No.: 14/073,928

(22) Filed: Nov. 7, 2013

(65) Prior Publication Data

US 2014/0179654 A1    Jun. 26, 2014

Related U.S. Application Data

(62) Division of application No. 12/671,932, filed as application No. PCT/EP2008/059702 on Jul. 24, 2008, now Pat. No. 8,785,427.

(30) Foreign Application Priority Data

Aug. 3, 2007  (IT) .............................. MI2007A1616

(51) Int. Cl.

| A61K 31/573 | (2006.01) |
|---|---|
| C07J 5/00 | (2006.01) |
| C12P 33/00 | (2006.01) |
| C07J 7/00 | (2006.01) |
| A61K 9/00 | (2006.01) |
| A61K 47/10 | (2006.01) |
| A61K 47/14 | (2006.01) |

(52) U.S. Cl.
CPC ........... *A61K 31/573* (2013.01); *A61K 9/0014* (2013.01); *A61K 47/10* (2013.01); *A61K 47/14* (2013.01); *C07J 5/0053* (2013.01); *C07J 7/008* (2013.01); *C12P 33/005* (2013.01); *C07B 2200/13* (2013.01)

(58) Field of Classification Search
CPC ..................... C07B 2200/13; C07J 7/008
USPC .......................................... 552/595; 514/177
See application file for complete search history.

(56) References Cited

U.S. PATENT DOCUMENTS

| 2,985,650 | A | 5/1961 | Batres et al. |
|---|---|---|---|
| 3,152,154 | A | 10/1964 | Ercoli et al. |
| 3,431,173 | A | 3/1969 | van der Waard et al. |
| 3,530,038 | A | 9/1970 | de Flines et al. |
| 3,780,177 | A | 12/1973 | Ercoli et al. |
| 4,645,763 | A | 2/1987 | Annen et al. |
| 4,670,427 | A | 6/1987 | Annen et al. |
| 5,264,428 | A | 11/1993 | Streber |
| 2005/0227994 | A1 | 10/2005 | Gemba et al. |
| 2012/0149671 | A1 | 6/2012 | Ajani et al. |
| 2014/0154306 | A1 | 6/2014 | Ajani et al. |

FOREIGN PATENT DOCUMENTS

| AU | 729928 B2 | 2/2001 |
|---|---|---|
| DE | 196 53 730 A1 | 6/1998 |
| EP | 791771 | 3/1958 |
| JP | 52010489 | 1/1977 |
| JP | 59-106500 A | 6/1984 |
| JP | 60-161998 A | 8/1985 |
| JP | 2004-530703 A | 10/2004 |
| JP | 2005-504762 | 2/2005 |
| JP | 2005-539016 A | 12/2005 |
| WO | WO 02/094843 A1 | 11/2002 |
| WO | WO 03/014141 A1 | 2/2003 |
| WO | WO 03/080042 A1 | 10/2003 |
| WO | WO 2004/014935 A1 | 2/2004 |
| WO | WO 2006/121097 A1 | 11/2006 |
| WO | WO 2007/014927 A2 | 2/2007 |
| WO | WO 2007/031349 A1 | 3/2007 |

OTHER PUBLICATIONS

Notice of Allowance, mailed Sep. 23, 2015 for U.S. Appl. No. 14/474,765, Ajani, M., et al., filed Sep. 2, 2014.
Byrn, S., et al., "Pharmaceutical Solids: A Strategic Approach to Regulatory Considerations," *Pharmaceutical Research* 12(7):945-954, Plenum Publishing Company, United States (1995).
Annen, K., et al., "17-Pivalate in der Pregnanreihe," Liebigs Ann. Chem:705-711, Wiley-VCH Verlag GmbH & Co. KGaA, Germany (1983).
Baldessari et al., "86. Lipase-Catalysed Regioselective Deacetylation of Androstane Derivatives," Helvetica Chimica Acta 79 (1996).
Belieu, R.M., "Mastodynia," Obstetrics and Gynecology Clinics of North America 21(3):461-477, W.B. Saunders Company, United States (1994).
Biollaz, von M. and Kalvoda, J., "263. Reaktionen von Steroiden mit Dialkylaminoschwefeltrifluoriden. I. 11β-Hydroxysteroide." Helvetica Chimica Acta 60(8):2703-2710, Schweizerische Chemische Gesellschaft, Switzerland (1977).
Bruttomesso, et al., "Lipase-catalysed deacetylation of androstane and pregnane dcrirativcs: influence of ring D substitution," Journal of Molecular Catalysis B: Ensymatic 29:149-153 (2004).
Caira, M.R., "Crystalline Polymorphism of Organic Compounds," in Topics in Current Chemistry, vol. 198, de Meijere, A., et al., Eds., pp. 164-208, Springer-Verlag, Germany (1998).
Celasco, et al., "Biological Profile of Cortexolone 17μ—Propionate (CB-03-01), a New Topical and Peripherally Selective Androgen Antagonist," Arzneim. Forsch./ Drug Res 54(12):881-886 (2004).
Cheung, et al., "Resistance to enzymic hydrolysis as a parameter in drug potency," International Journal of Pharmaceuticals 27:325-333 (1985).

(Continued)

*Primary Examiner* — Barbara P Badio
(74) *Attorney, Agent, or Firm* — Sterne, Kessler, Goldstein & Fox P.L.L.C.

(57) ABSTRACT

The present invention refers to a new enzymatic process for obtaining 17α-monoesters of cortexolone and/or its 9,11-dehydroderivatives starting from the corresponding 17α,21-diesters which comprises an enzymatic alcoholysis reaction. Furthermore, the present invention refers to new crystalline forms of cortexolone 17α-propionate and 9,11-dehydro-cortexolone 17α-butanoate.

24 Claims, 28 Drawing Sheets

(56) References Cited

OTHER PUBLICATIONS

Ferraboschi, et al., "Lipase-catalyzed preparation of corticosteroid 17μ-esters endowed with antiandrogenic activity," Tetrahedron Letters 49:4610-4612 (2008).

Ford, J.L. and Timmins, P., Eds., "Ch. 6 Thermal analysis in the characterization of pharmaceutical solids," in Pharmaceutical Thermal Analysis: Techniques and Applications, pp. 139-140, Ellis Horwood Limited, England (1989).

Franssen, et al., "Enzymatic alcoholysis of alkoxymethyl alkanoates: a possibile approach for the kinetic resolution of tertiary alcohols," Tetrahedron Letters 39:8345-8348 (2004).

Gardi, R., et al., "52. Derivati di condensazione nella catena laterale di corticosteroidi.—Nota III. Preparazione e reazioni dei 17-monesteri," Gazz. Chim. It. 93:431-450, Palermo, Italy (1963).

Gardi, R., et al., "Corticosteroid 17α-Monoesters from 17α,21-Cyclic Orthoesters," Tetrahedron Letters 13:448-451, Pergamon Press Ltd., Great Britain (1961).

Hilfiker, R., Ed., "Characterization of Polymorphic Systems Using Thermal Analysis," in Polymorphisms in the Pharmaceutical Industry, pp. 46-48, Wiley-VCH Verlag GmbH & Co. KGaA, Germany (2006).

Meriggiola, M.C. and Pelusi, G., "Advances in male hormonal contraception," Expert Opin. Investig. Drugs 15(4):389-397, Ashley Publications, England (2006).

Misaki, et al., "Enzymic hydrolysis of hydrocoristone diesters in skin," Yakuzaigaku No. 42(2), Abstract. Caplus Chemical Abstract Service Database Accession No., 1982:575-431.

Morrison, R.T. and Boyd, R.N., Eds., "Chap. 20 Functional Derivatives of Carboxylic Acids," in Organic Chemistry, Sixth Edition, pp. 764-766, Prentice-Hall, Inc., Englewood Cliffs, New Jersey, United States (1992).

Schinzer, W.C., et al., "Characterization and Interconversion of Polymorphs of Premafloxacin, a New Quinolone Antibiotic," Journal of Pharmaceutical Sciences 86(12):1426-1431, American Chemical Society and American Pharmaceutical Association, United States (1997).

Tuladhar, M.D., et al., "Thermal behaviour and dissolution properties of phenylbutazone polymorphs," J. Pharm. Pharmcol. 35:208-214, Pharmaceutical Society of Great Britain, England (1983).

Turner, R.B., "Acylation of 17-Hydroxy-20-ketosteroids," J. Am. Chem. Soc. 75:3489-3492, American Chemical Society, United States (1953).

Voigt, W. and Hsia, S.L., "The Antiandrogenic Action of 4-Androsten-3-one-17β-Carboxylic Acid and Its Methyl Ester on Hamster Flank Organ," Endocrinology 92(4):1216-1222, Endocrine Society, United States (1973).

Japanese Office Action for Application No. 2010-518628 dated Feb. 8, 2013.

Non-Final Office Action, mailed Sep. 25, 2006 for U.S. Appl. No. 10/486,386, filed Sep. 16, 2004.

Final Office Action, mailed Apr. 13, 2007 for U.S. Appl. No. 10/486,386, filed Sep. 16, 2004.

Non-Final Office Action, mailed Sep. 7, 2007 for U.S. Appl. No. 10/486,386, filed Sep. 16, 2004.

Final Office Action, mailed Mar. 21, 2008 for U.S. Appl. No. 10/486,386, filed Sep. 16, 2004.

Non-Final Office Action, mailed Jul. 10, 2008 for U.S. Appl. No. 10/486,386, filed Sep. 16, 2004.

Final Office Action, mailed Feb. 27, 2009 for U.S. Appl. No. 10/486,386, filed Sep. 16, 2004.

Non-Final Office Action, mailed Jul. 13, 2011 for U.S. Appl. No. 12/457,870, filed Jun. 24, 2009.

Non-Final Office Action, mailed Apr. 24, 2014 for U.S. Appl. No. 14/103,707, filed Dec. 11, 2013.

Description: Cortexolone 17 alpha-propionate CB-03-01 methylterbutylether
Comments: Tablet in KBr without vacuum Description: Cortexolone 17 alpha-propionate CB-03-01 diisopropylether Description: Cortexolone 17 alpha-propionate batch CB-03-01
Comments: Tablet in KBr without vacuum Description: ACETONE HEXANE
— 9-DEHYDROCORTEXOLONE 17 ALPHA-BUTIRRATE ACETONE-HEXANE
Comments: Tablet in KBr without vacuum dil. 1:100

ENZYMATIC PROCESS FOR OBTAINING 17α-MONOESTERS OF CORTEXOLONE AND/OR ITS 9,11-DEHYDRODERIVATIVES

Cortexolone derivatives in which the hydroxyl group at position C-17α is esterified with short chain aliphatic or aromatic acids, and the derivatives of the corresponding 9,11-dehydro derivative, are known to have an antiandrogenic effect.

EP1421099 describes cortexolone 17α-propionate and 9,11-dehydro-cortexolone-17-α-butanoate regarding a high antiandrogenic biological activity demonstrated both "in vitro" and "in vivo" on the animal.

A method for obtaining the above mentioned derivatives is described by Gardi et al. (Gazz. Chim. It. 63, 43 1, 1963) and in U.S. Pat. No. 3,152,154 providing for the transformation of cortexolone, or transformation of 9,11-dehydro-cortexolone, in the intermediate orthoester using orthoesters available in the market as a mixture of aprotic solvents such as cyclohexane and DMF, in presence of acid catalysis (ex. PTSA.H₂O). The intermediate orthoester thus obtained can be used as is or upon purification by suspension in a solvent capable of solubilizing impurities, preferably in alcohols. The subsequent hydrolysis in a hydroalcoholic solution, buffered to pH 4-5 preferably in acetate buffer, provides the desired monoester.

Such synthesis is indicated in the diagram 1 below.

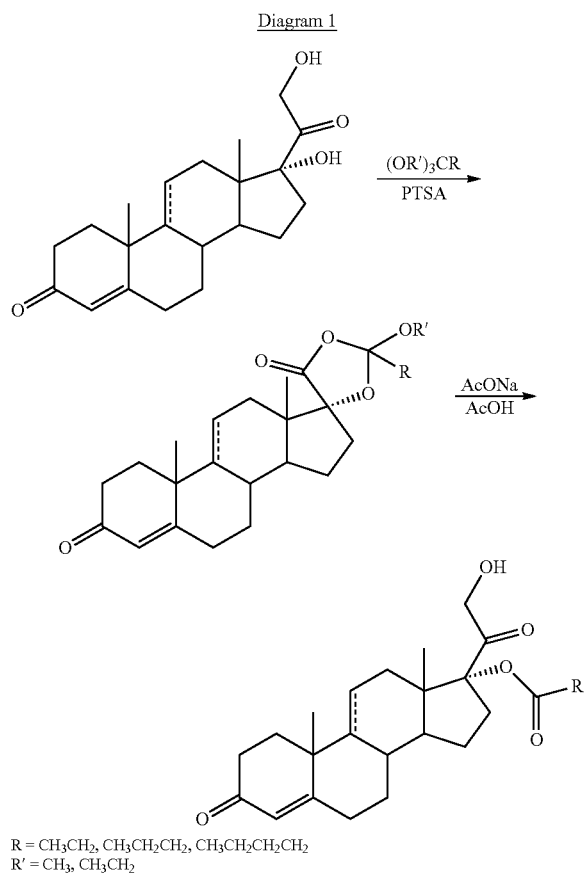

Diagram 1

R = CH₃CH₂, CH₃CH₂CH₂, CH₃CH₂CH₂CH₂
R' = CH₃, CH₃CH₂

However, the monoesters thus obtained were, in the reaction conditions, unstable and, consequently hard to manipulate and isolate (R. Gardi et at Tetrahedron Letters, 448, 1961). The instability is above all due to the secondary reaction of migration of the esterifying acyl group from position 17 to position 21.

It is thus known that in order to obtain the above mentioned monoesters with a chemical purity in such a manner to be able to proceed to the biological tests, it is necessary to use, at the end of the synthesis, a purification process which is generally performed by means of column chromatography.

Furthermore, U.S. Pat. No. 3,152,154 describes how the hydrolysis of the diester in a basic environment is not convenient due to the formation of a mixture of 17α,21-diol, of 17- and 21-monoesters, alongside the initial non-reacted product.

Now, it has been surprisingly discovered that an alcoholysis reaction using a lipase from *Candida* as a biocatalyst can be usefully applied during the preparation of 17α monoesters of cortexolone, or its 9,11-dehydroderivatives.

As a matter of fact, it has been discovered that such enzymatic alcoholysis of the 17,21-diester of the cortexolone, or of its derivative 9,11-dehydro, selectively occurs in position 21 moving to the corresponding monoester in position 17, as shown in diagram 2 below:

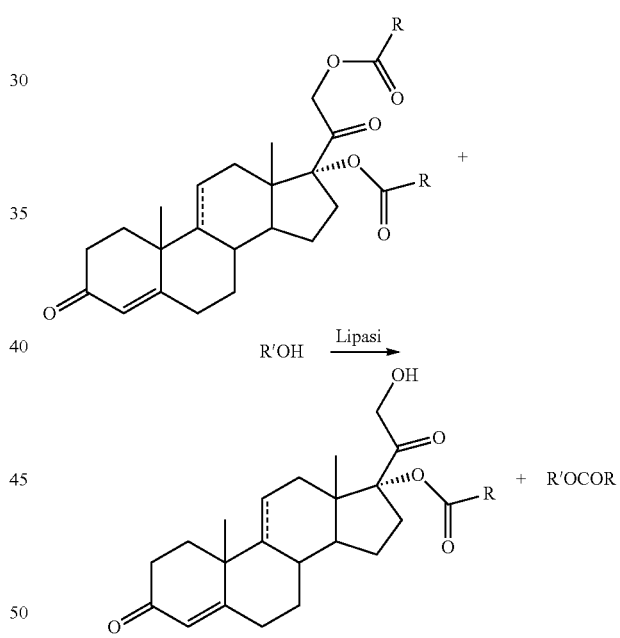

Diagram 2

The chemoselectivity of the special enzymatic reaction in alcoholysis conditions, according to the present invention, opens new perspectives for preparation, at industrial level with higher yields, of 17α-monoesters with respect to the methods already indicated in literature.

The diesters serving as a substrate for the reaction of the invention can be prepared according to the prior art, for example following the one described in B. Turner, (Journal of American Chemical Society, 75, 3489, 1953) which provides for the esterification of corticosteroids with a linear carboxylic acid in presence of its anhydride and PTSA monohydrate.

Therefore, an object of the present invention is a process for the preparation of 17α monoesters of cortexolone, and its 9,11-dehydroderivatives, of formula I.

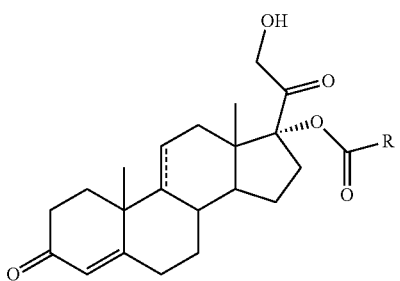

wherein R is a linear or branched aliphatic or aromatic chain containing 1 to 10 carbon atoms, characterized in that a compound of formula II

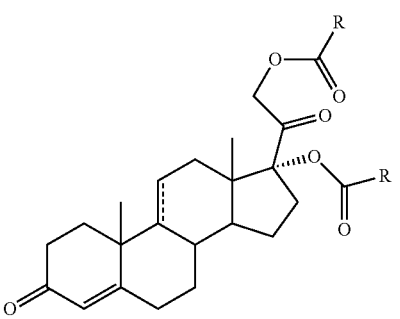

wherein R bears the same meaning indicated above, is reacted with a compound having the formula R'OH, wherein R' is a linear chain containing 1 to 10 carbon atoms, preferably a $C_1$-$C_8$ alkyl, in presence of a lipase from *Candida*. According to the present invention R is preferably a $C_1$-$C_4$ alkyl, even more preferably it is selected from among $CH_3$, $CH_3CH_2$, $CH_3(CH_2)_2$ or $CH_3(CH_2)_3$.

The dashed symbol in position 9,11 inside the abovementioned formulas I and II means that the double bond can be present (9,11-dehydroderivative) or not present in such position, as shown in the formulas indicated hereinafter

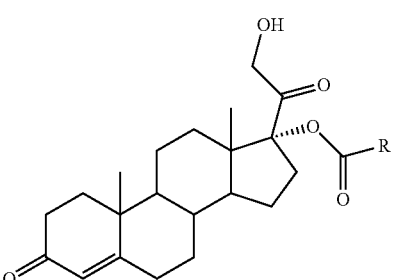

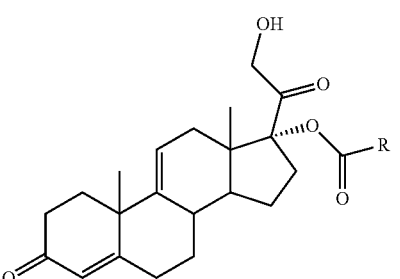

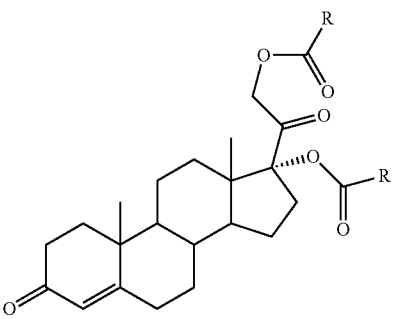

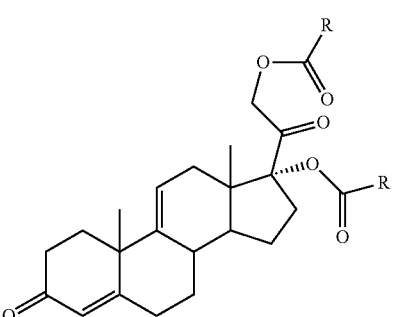

Figure 1:
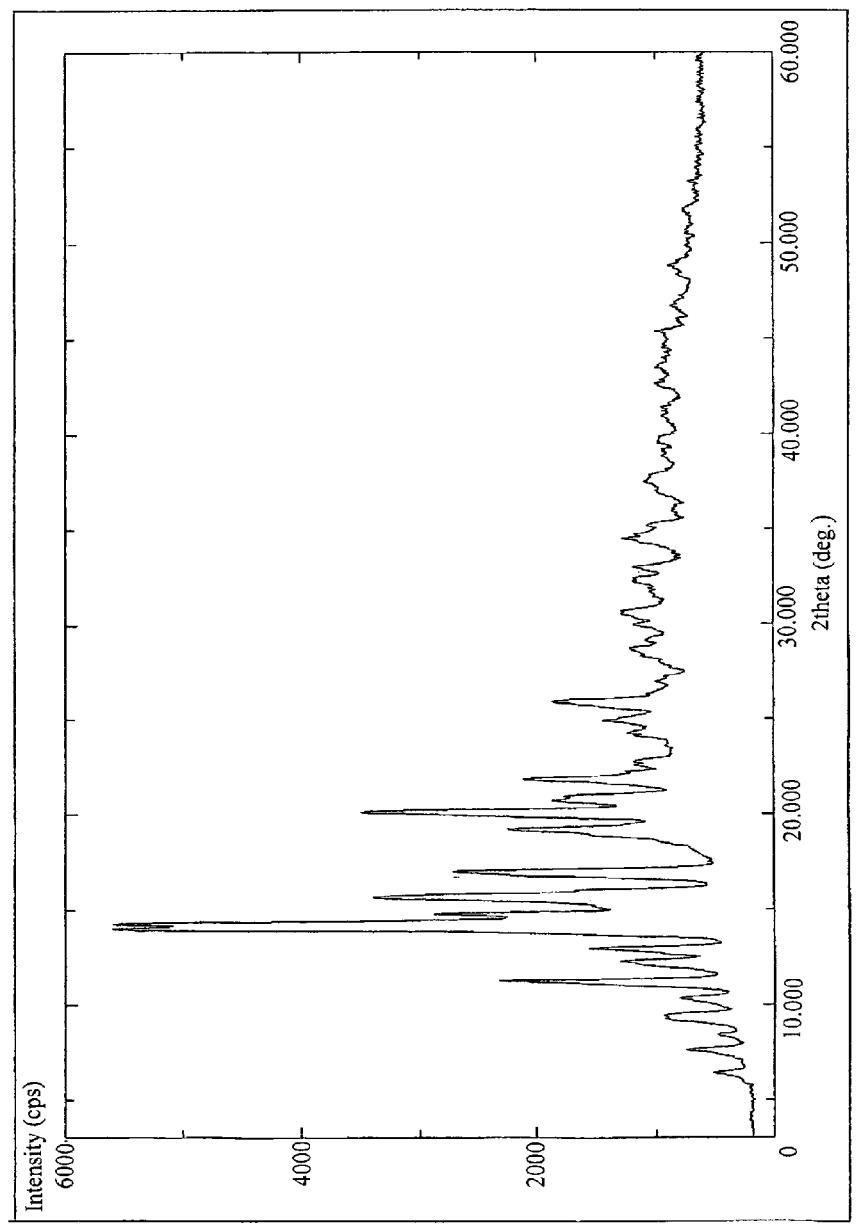
FIG. 1 shows a DRX spectrum of crystalline form I of cortexolone-17α-propionate.

The lipase from *Candida* used to catalyze the process of the present invention is preferably selected between the lipase from *Candida cylindracea* (CCL) and lipase from *Candida antarctica* of type B (CALB).

Lipase from *Candida*, and in particular the ones from *Candida cylindracea* and *Candida antarctica* are proved to be capable of selectively hydrolyzing the ester function in position 21, contrary to the porcine pancreatic lipase (PPL) and to one from *Pseudomonas fluorescens* (PFL), which are proved to be almost inactive.

The concentration of the initial diesters of formula II is preferably in the range of about 0.01 to 0.15 molar, more preferably about 0.025 molar.

The process of the invention preferably occurs in the presence of an organic solvent, more preferably an aprotic organic solvent.

Said solvent is then preferably selected from among toluene, acetonitrile, tetrahydrofuran, dichloromethane and/or chloroform.

The R'OH alcohol according to the invention is preferably selected from among methanol, ethanol, butanol and/or octanol.

Said alcohol is preferably present at a quantity in the range of about 0.5 to about 50 moles per mole of initial substrate, more preferably 5 moles per mole of substrate.

The process according to the present invention preferably occurs under constant stirring until the initial diester of formula II is dissolved. Subsequently the enzyme used is removed for filtration, preferably filtration on Celite and the monoester of formula I is obtained through evaporation of the solvent under low pressure.

When the compound of formula II is a 17α,21-diester of cortexolone, the reaction time of the process is usually in the range of 20 to 150 hours, preferably in the range of 24 to 72 hours and the reaction temperature is preferably in the range of about 10 to 48° C., more preferably in the range of 20 to 32° C.

Table I below summarizes the reaction conditions and the results of the enzymatic alcoholysis according to the present invention.

TABLE I

Enzymatic alcoholysis reaction of 17α,21-diesters of cortexolone to produce the corresponding 17α-monoester.

| Compound of formula II (diester) | Enzyme | Alcohol | Solvent | Reaction time (hours) | Yield of the monoester of formula I* |
|---|---|---|---|---|---|
| Diacetate | CCL | Octanol | Toluene | 51 | 97% |
| | CALB | Ethanol | Toluene | 96 | 67% |
| | CALB | Octanol | Acetonitrile | 51 | 88% |
| Dipropionate | CCL | Ethanol | Toluene | 120 | 73% |
| | CCL | Butanol | Toluene | 24 | 100% |
| | CCL | Octanol | Toluene | 28 | 100% |
| | CCL | Butanol | Acetonitrile | 96 | 91% |
| | CCL | Butanol | Tetrahydrofuran | 96 | 86% |
| | CCL | Butanol | Chloroform | 96 | 10% |
| | PPL | Octanol | Toluene | 120 | 13% |
| | PFL | Methanol | Chloroform | 24 | 0% |
| | CALB | Octanol | acetonitrile | 76 | 91% |
| Dibutanoate | CCL | Toluene | Butanol | 74 | 98% |
| | CCL | Toluene | Octanol | 24 | 98% |
| Divalerate | CCL | Toluene | Butanol | 74 | 81% |
| | CCL | Toluene | Octanol | 48% | 97% |

*the conversion percentages were evaluated from the $^1$H-NMR spectra from the integrations of signals due to the hydrogens in position 21 of the corresponding diesters and monoesters.

The amount of said enzyme, calculated with respect to the initial substrate, may vary depending on the type of enzyme used. In particular, said enzyme is preferably used in an amount in the range of 100 to 1,000,000 U/mmol; more preferably in the range of 1,000 to 1,000,000 U/mmol in case of CCL and in the range of 100 to 100,000 U/mmol in case of CALB. Even more preferably, said enzyme is present at an amount of about 60,000 U/mmol in case of CCL and about 5,000 U/mmol in case CALB.

Furthermore, from an economical/industrial point of view, the possibility to reutilize such enzymes in several cycles without losing the catalytic activity was proved.

The enzymatic method according to the present invention also proved useful not only for converting 17α-21-diesters of cortexolone or of 9,11-dehydro-cortexolone: in particular the 17α-butanoate of 9,11-dehydrocortexolone was obtained starting from the corresponding dibutanoate preferably using the CCL enzyme and methanol as an acceptor alcohol of the acyl group.

The concentration of the initial 9,11-dehydro derivatives is preferably in the range of 0.01 to 0.15 molar, more preferably 0.025 molar.

In this case, the reaction time is preferably in the range of 45 to 55 hours, preferably 53 hours.

Also in this case the reaction temperature is preferably in the range of 10 to 48° C., more preferably in the range of 20 to 32° C.

Table 2 below shows the reaction conditions of the enzymatic alcoholysis of 17α,21-dibutanoate of 9,11-dehydrocortexolone and the related final yield of the respective monoester.

TABLE 2

Enzymatic alcoholysis reaction of 17α,21-diesters of 9,11-dehydrocortexolone to produce the corresponding 17α-monoester.

| Compound of formula II (diester) | Enzyme | Alcohol | Solvent | Reaction time (hours) | Yield in compound of formula I* |
|---|---|---|---|---|---|
| Dibutanoate | CCL | Methanol | Toluene | 53 | 79% |
| Dibutanoate | CCL | Ethanol | Toluene | 53 | 28% |
| Dibutanoate | CCL | Butanol | Toluene | 53 | 100% |
| Dibutanoate | CCL | Octanol | Toluene | 53 | 100% |

*the conversion percentages were evaluated from the $^1$H-NMR spectra from the integrations of signals due to the hydrogens in position 21 of the corresponding diesters and monoesters.

Furthermore, the process according to the present invention may optionally comprise a final step of crystallization from an organic solvent, water, buffered aqueous solutions and/or or their mixture.

The organic solvent of said step of crystallization is preferably selected from among diisopropylether, tert-butylmethylether, dichloromethane, ethyl acetate, hexane, acetone, ethanol, water or their mixture at any proportion.

Thus, further object of the present invention are crystalline forms of 17α-monoesters of cortexolone, and their corresponding 9,11-dehydro derivatives.

In particular, an object of the present invention are the crystalline forms of cortexolone 17α-propionate and of 9,11-cortexolone-17α-butanoate.

Figure 2:
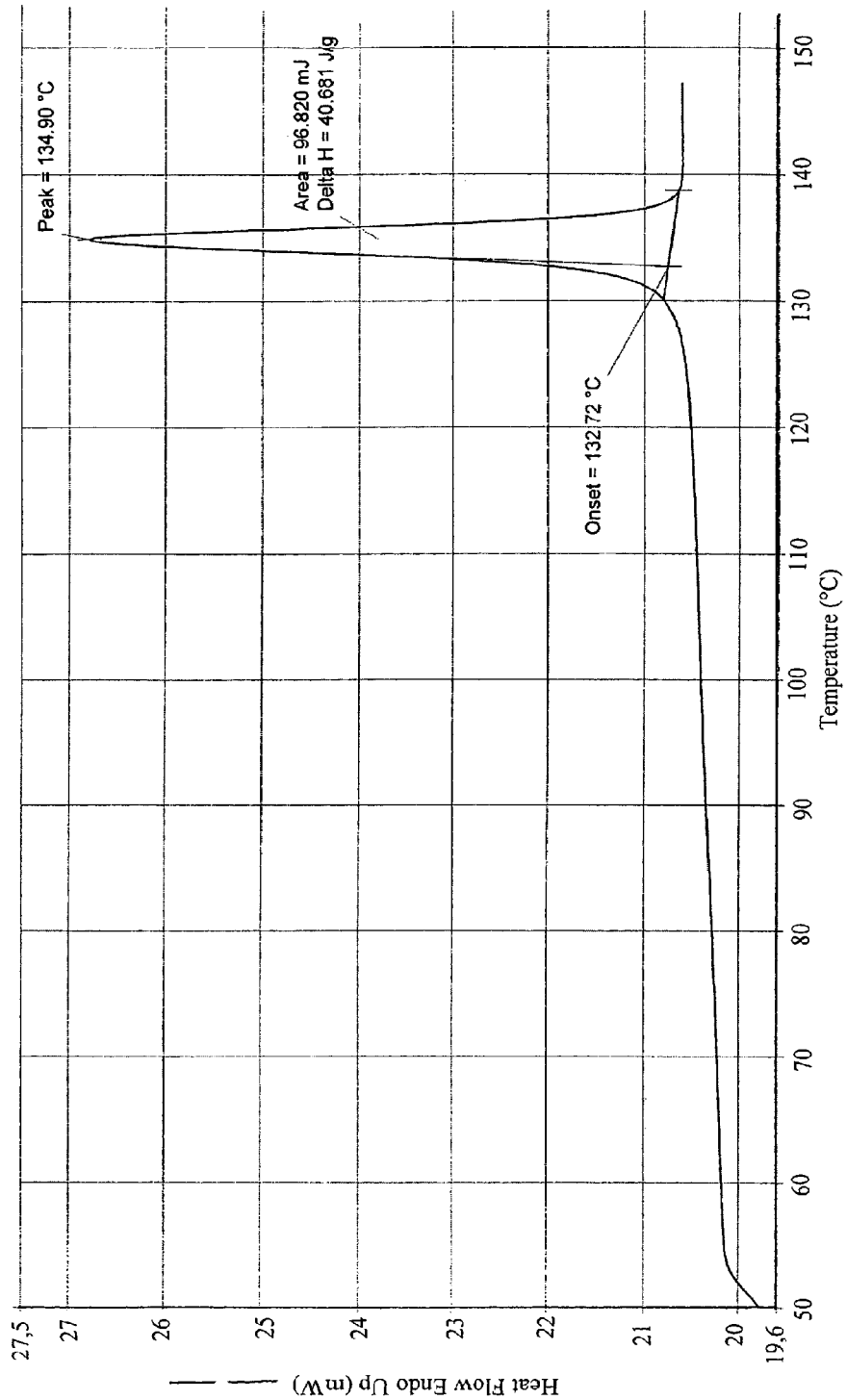
FIG. 2 shows a DSC spectrum of crystalline form I of cortexolone-17α-propionate.
Figure 3:
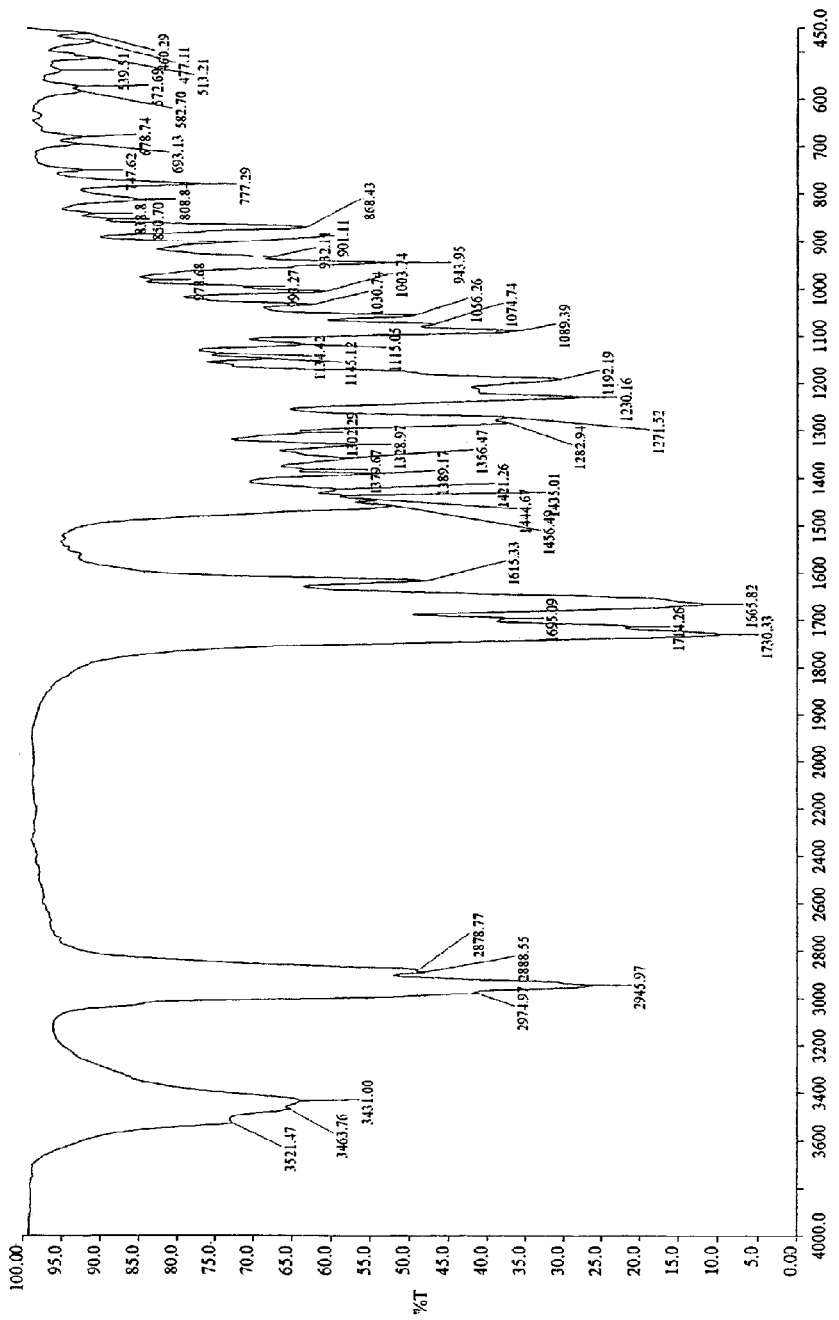
FIG. 3 shows an IR spectrum of crystalline form I of cortexolone-17α-propionate.

The crystalline form I of 17α-propionate is preferably obtained through crystallization from tert-butylmethylether. The concentration of 17α-propionate in said solvent is in the range of 0.9 to 1.1 g in 9-11 ml of tert-butylmethylether preferably 1 g in 10 ml. Said crystalline form I is characterized by a melting point in the range of about 133 to 135° C. and/or a DRX as in FIG. 1 and/or a DSC as shown in FIG. 2 and/or an IR as shown in FIG. 3.

The crystalline form II of 17α-propionate is preferably obtained through crystallization from diisopropylether. The concentration in said solvent is preferably in the range of 0.9 to 1.1 g in 54-66 ml of diisopropylether.

Figure 4:
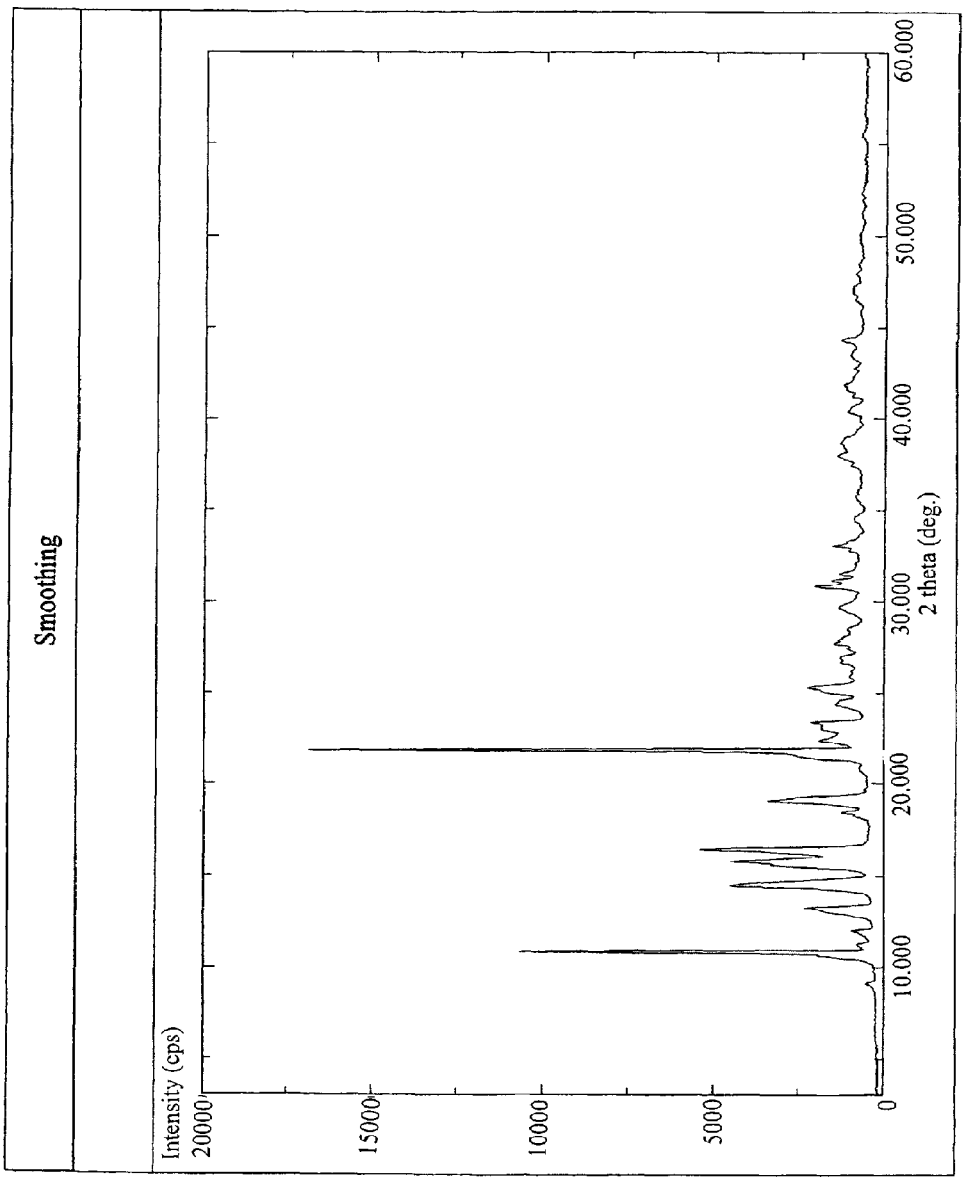
FIG. 4 shows a DRX spectrum of crystalline form II of cortexolone-17α-propionate.
Figure 5:
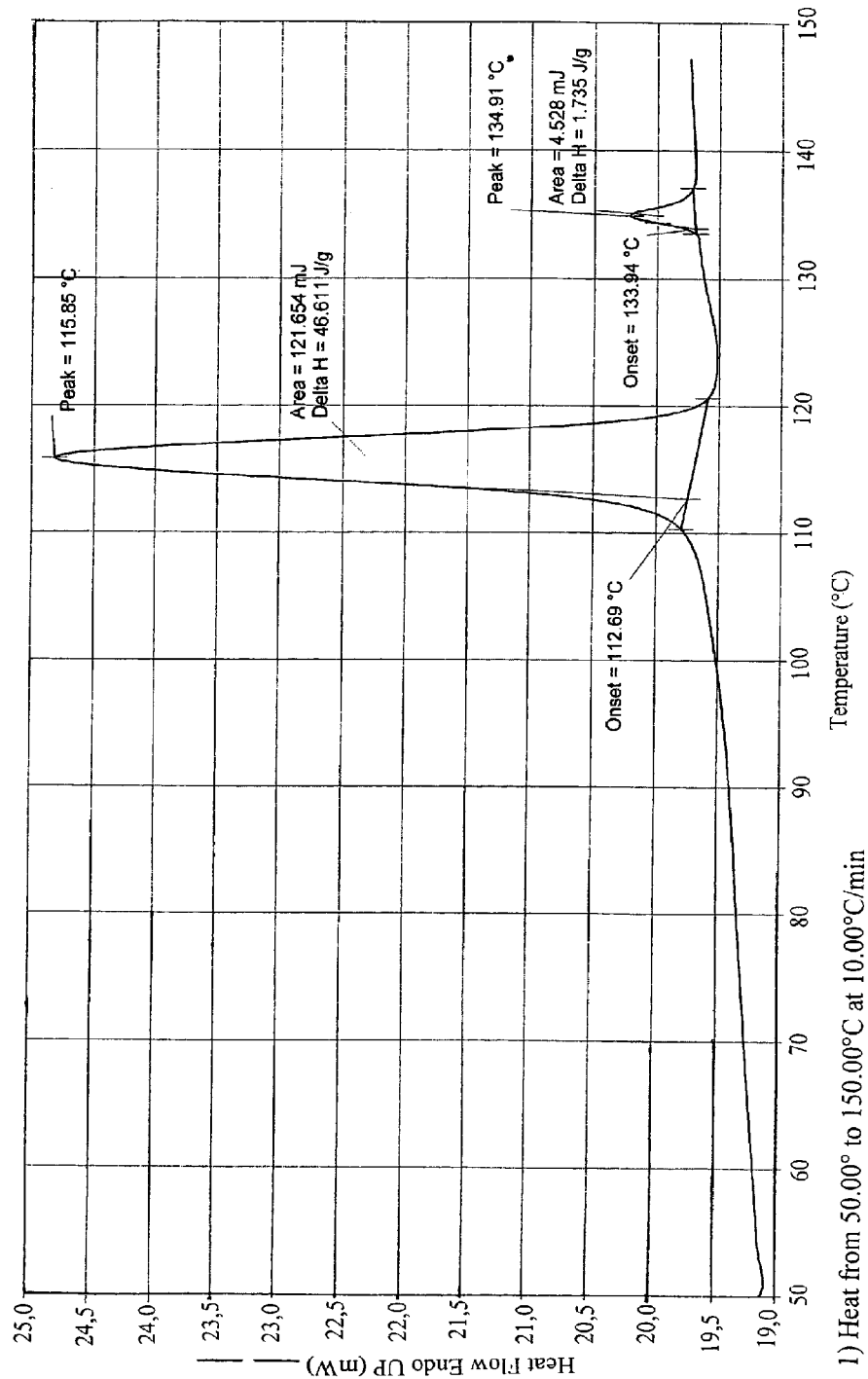
FIG. 5 shows a DSC spectrum of crystalline form II of cortexolone-17α-propionate.
Figure 6:
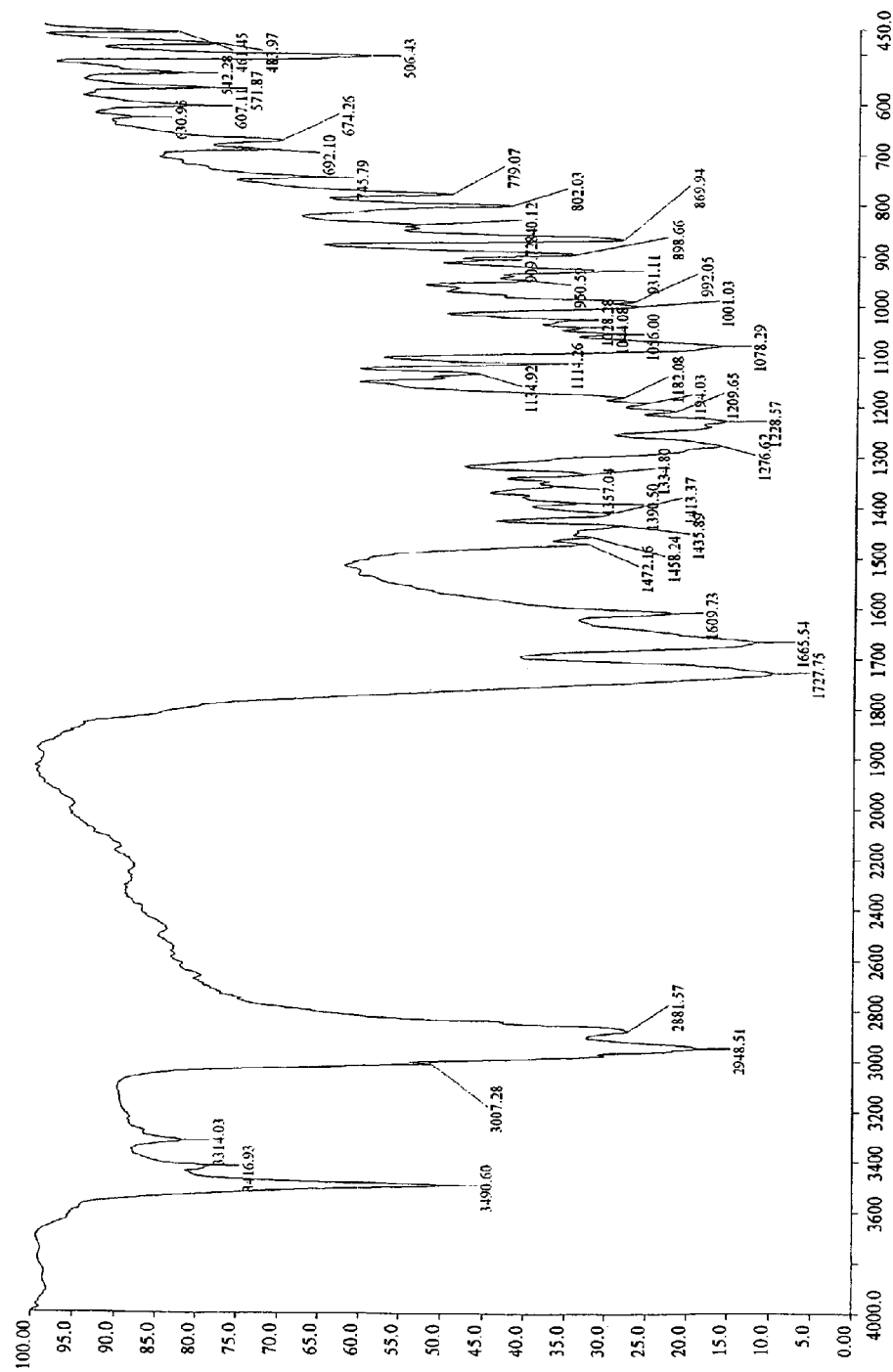
FIG. 6 shows an IR spectrum of crystalline form II of cortexolone-17α-propionate.

Said crystalline form II is characterized by a melting point in the range of about 114 to 116° C. and/or a DRX as in FIG. 4 and/or a DSC as shown in FIG. 5 and/or an IR as shown in FIG. 6.

The crystalline form III of 17α-propionate is preferably obtained through crystallization from a mixture of dichloromethane/n-hexane preferably in a ratio of about 1/30, acetone/n-hexane preferably in a ratio of about 1/8, or ethanol/water mixture preferably in a ratio of about 1/2.

The melting point of said crystalline forms III could not be determined.

Figure 7:
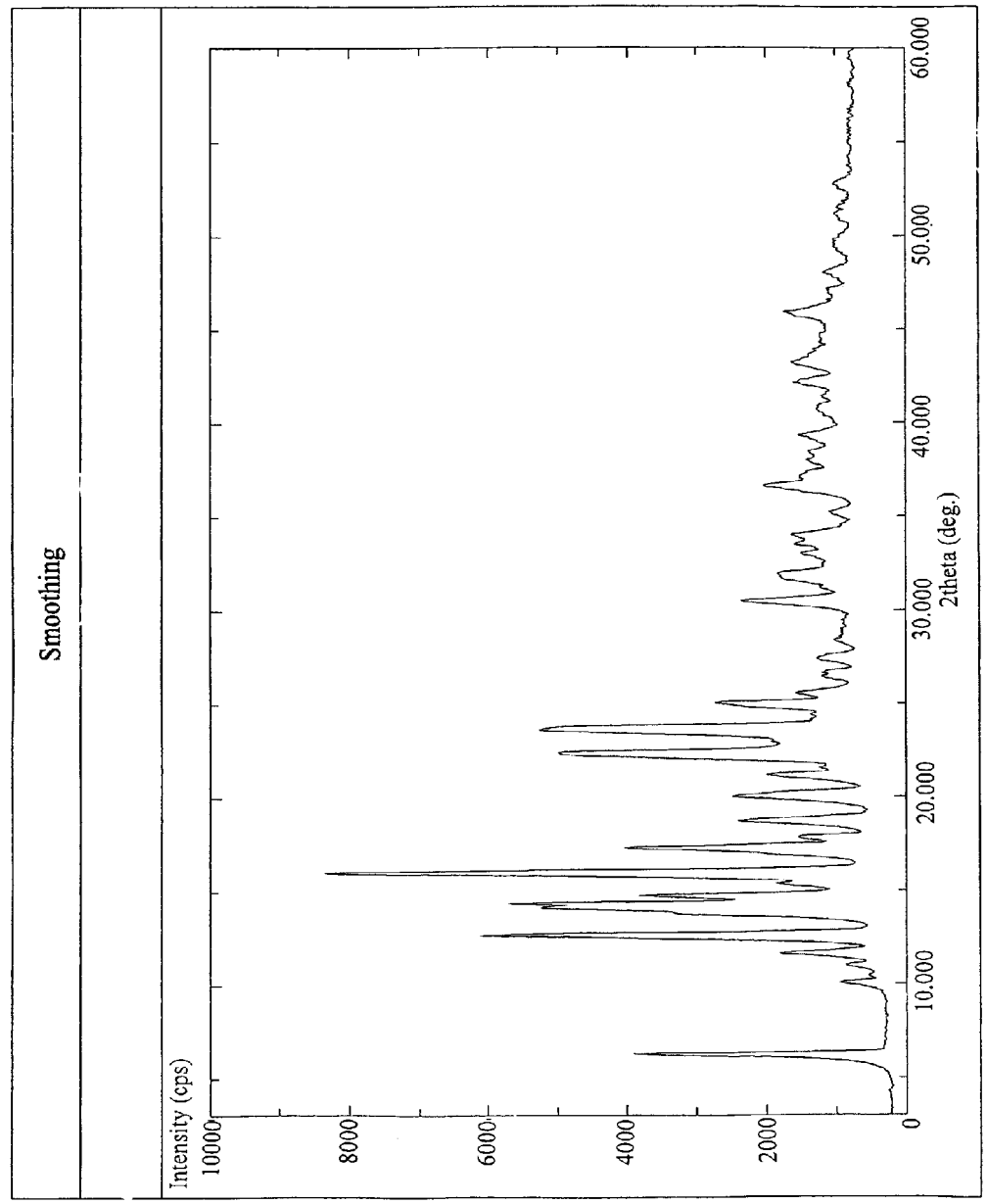
FIG. 7 shows a DRX spectrum of crystalline form III of cortexolone-17α-propionate.
Figure 8:
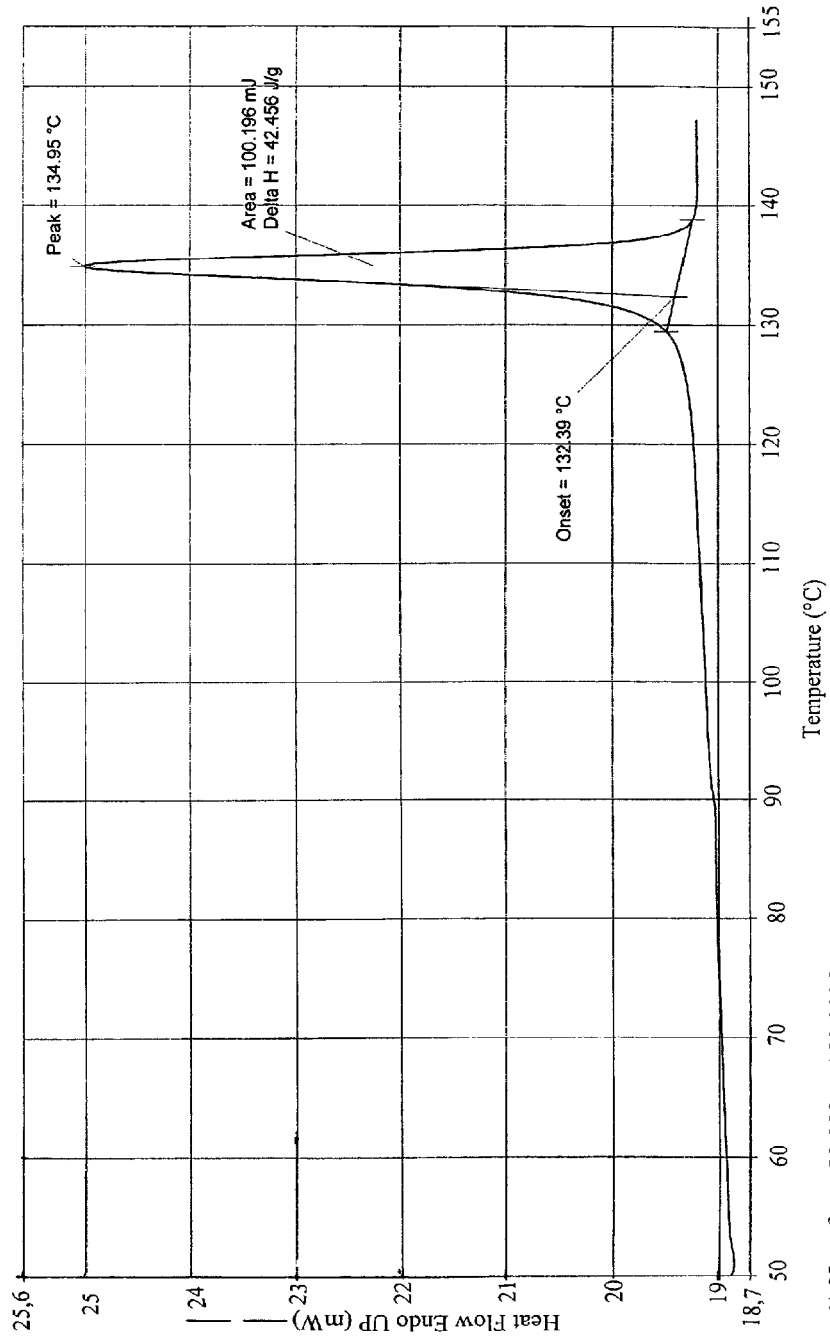
FIG. 8 shows a DSC spectrum of crystalline form III of cortexolone-17α-propionate.
Figure 9:
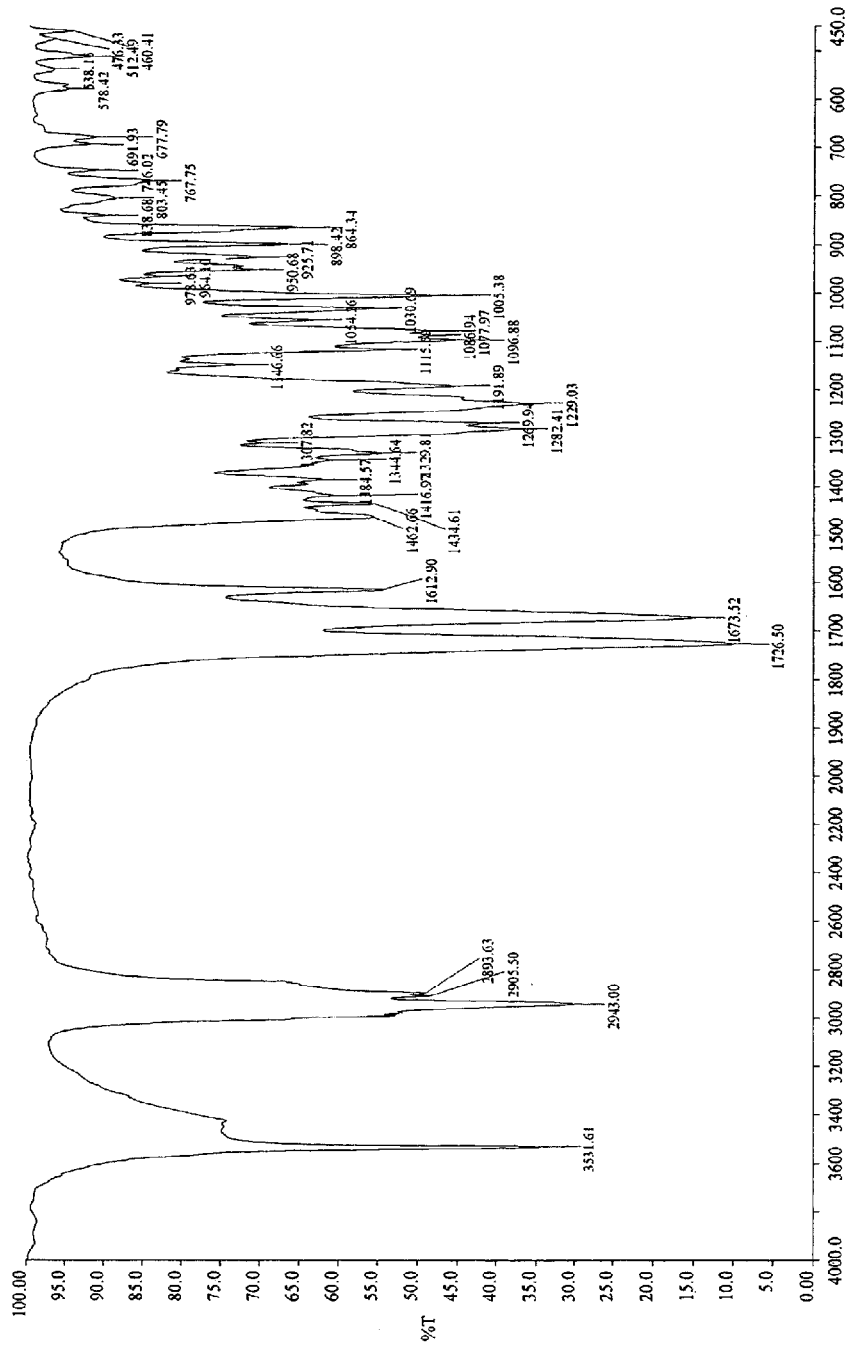
FIG. 9 shows an IR spectrum of crystalline form III of cortexolone-17α-propionate.
Figure 10:
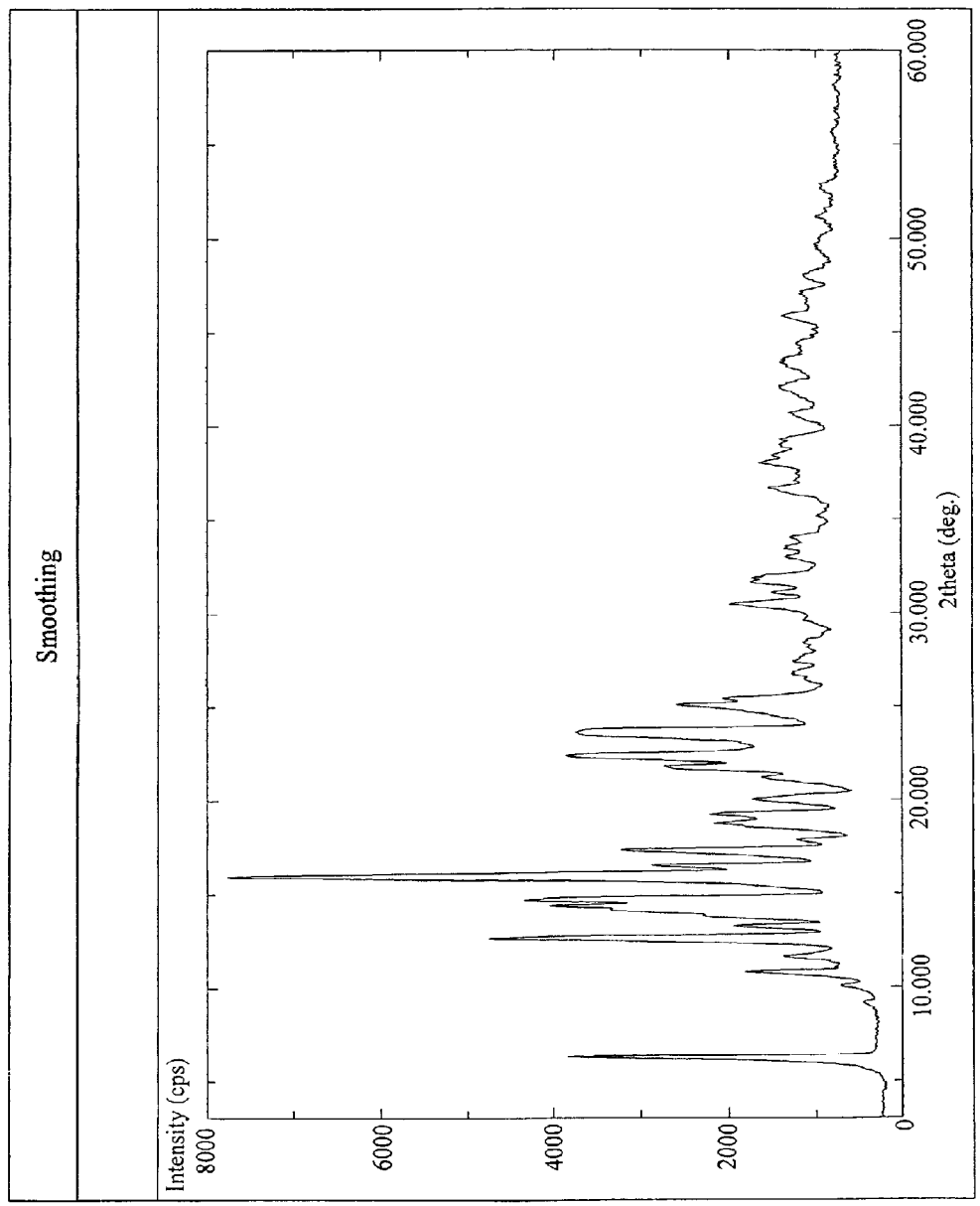
FIG. 10 shows a DRX spectrum of crystalline form III of cortexolone-17α-propionate.
Figure 11:
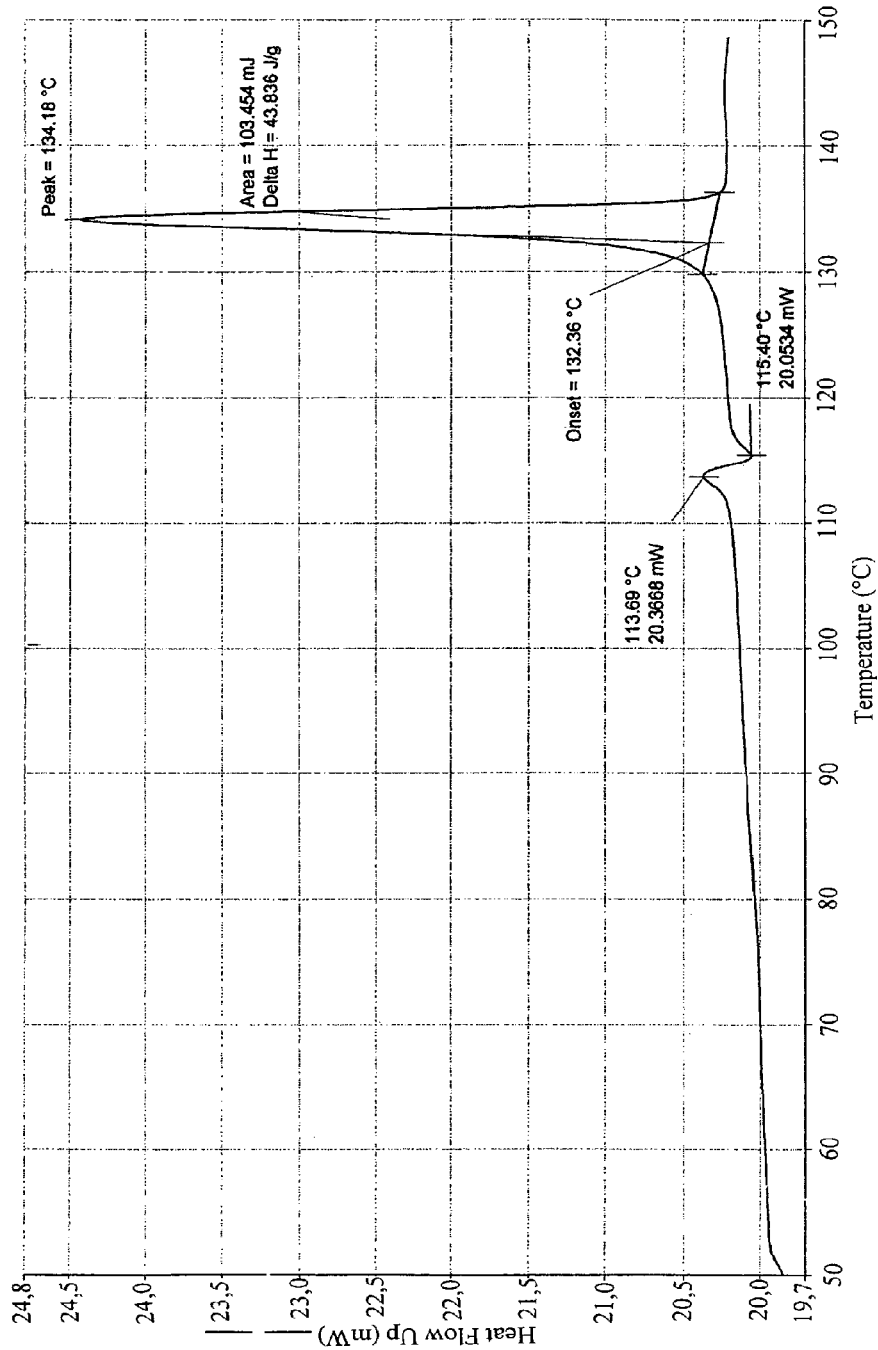
FIG. 11 shows a DSC spectrum of crystalline form III of cortexolone-17α-propionate.
Figure 12:
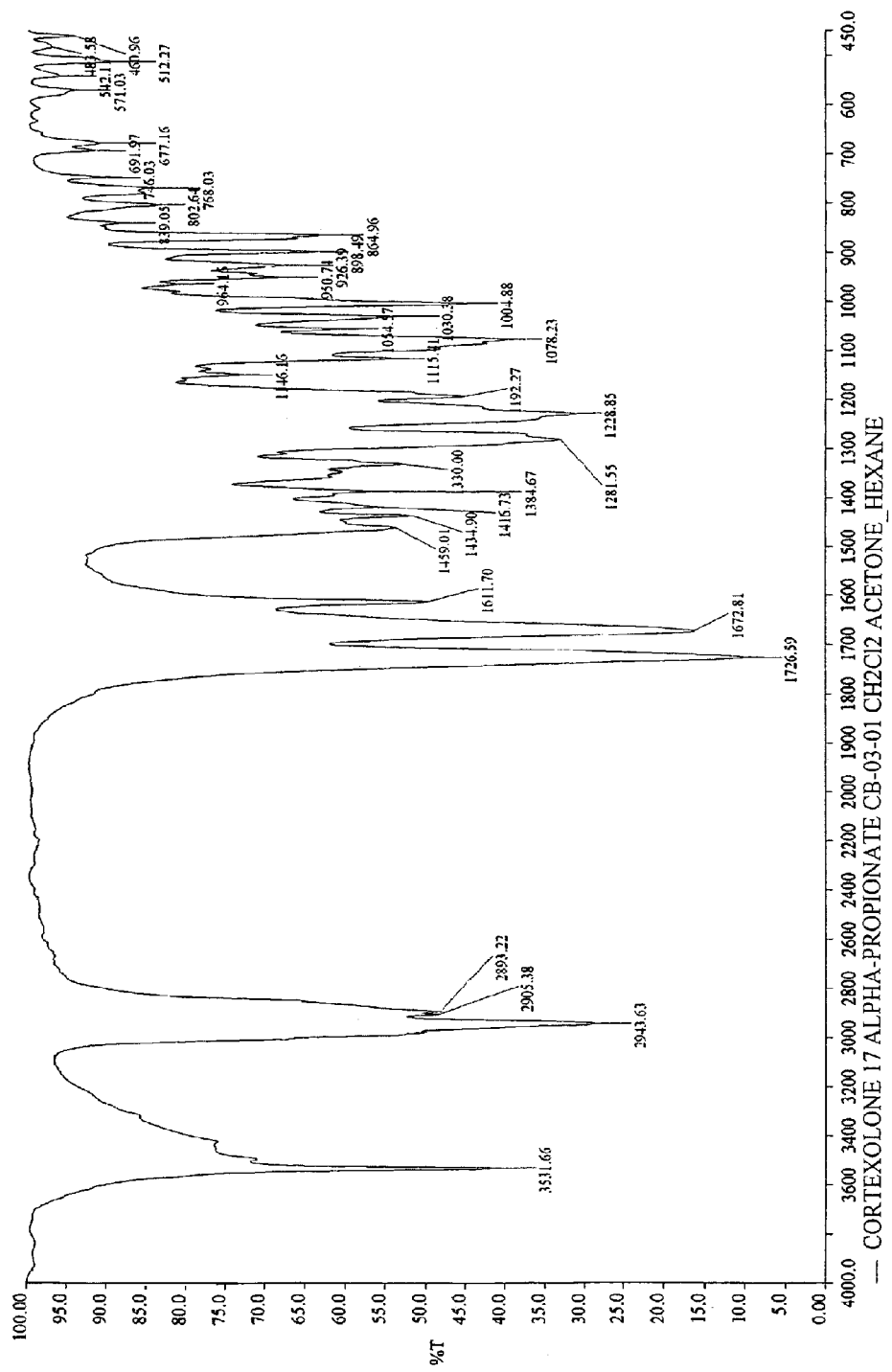
FIG. 12 shows an IR spectrum of crystalline form III of cortexolone-17α-propionate.

The crystalline form III obtained from dichloromethane/n-hexane has a DRX as shown in FIG. 7 and/or a DSC as shown in FIG. 8 and/or an IR as shown in FIG. 9. The crystalline form III obtained from acetone/n-hexane has a DRX as shown in FIG. 10 and/or a DSC as shown in FIG. 11 and/or an IR as shown in FIG. 12.

Figure 13:
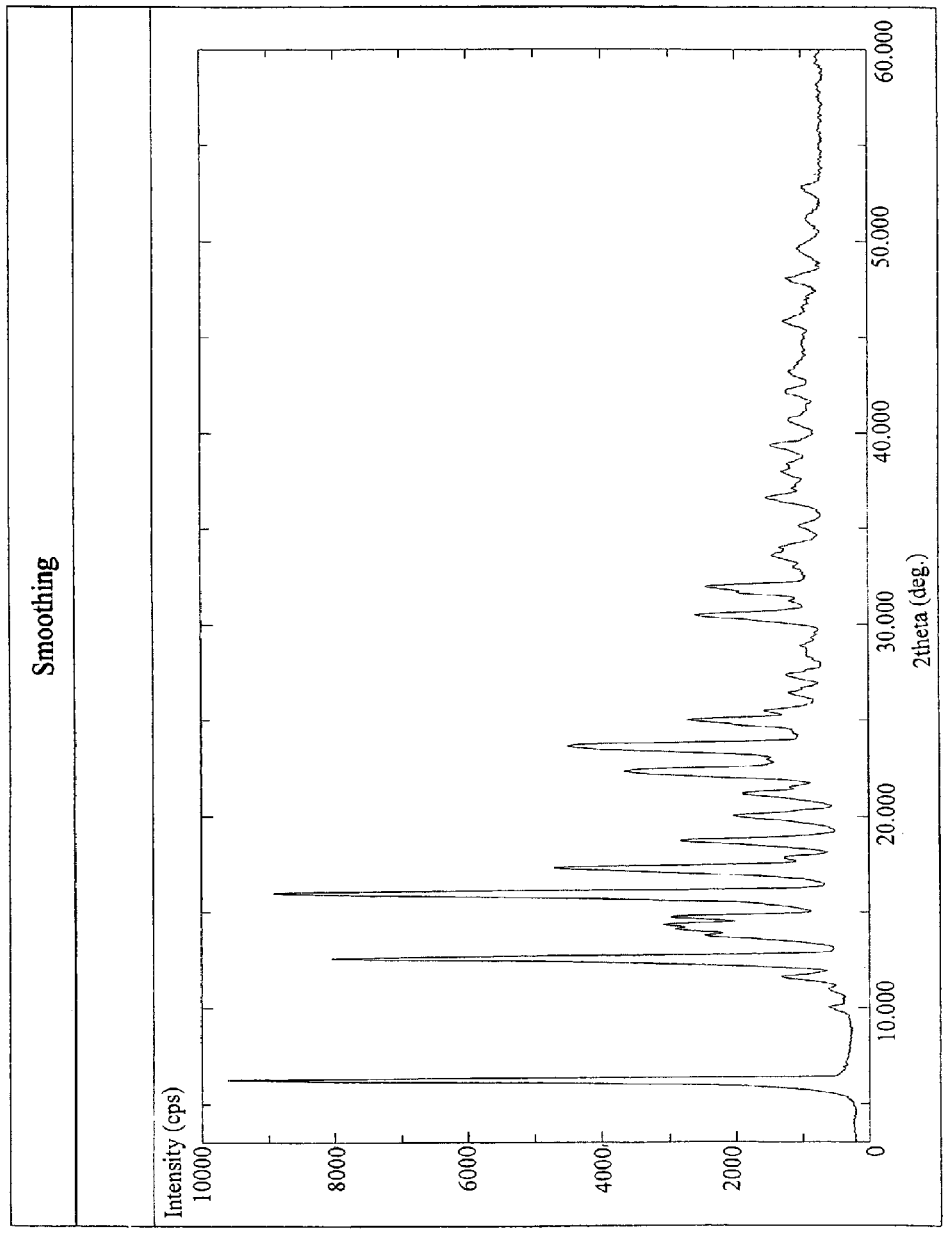
FIG. 13 shows a DRX spectrum of crystalline form III of cortexolone-17α-propionate.
Figure 14:
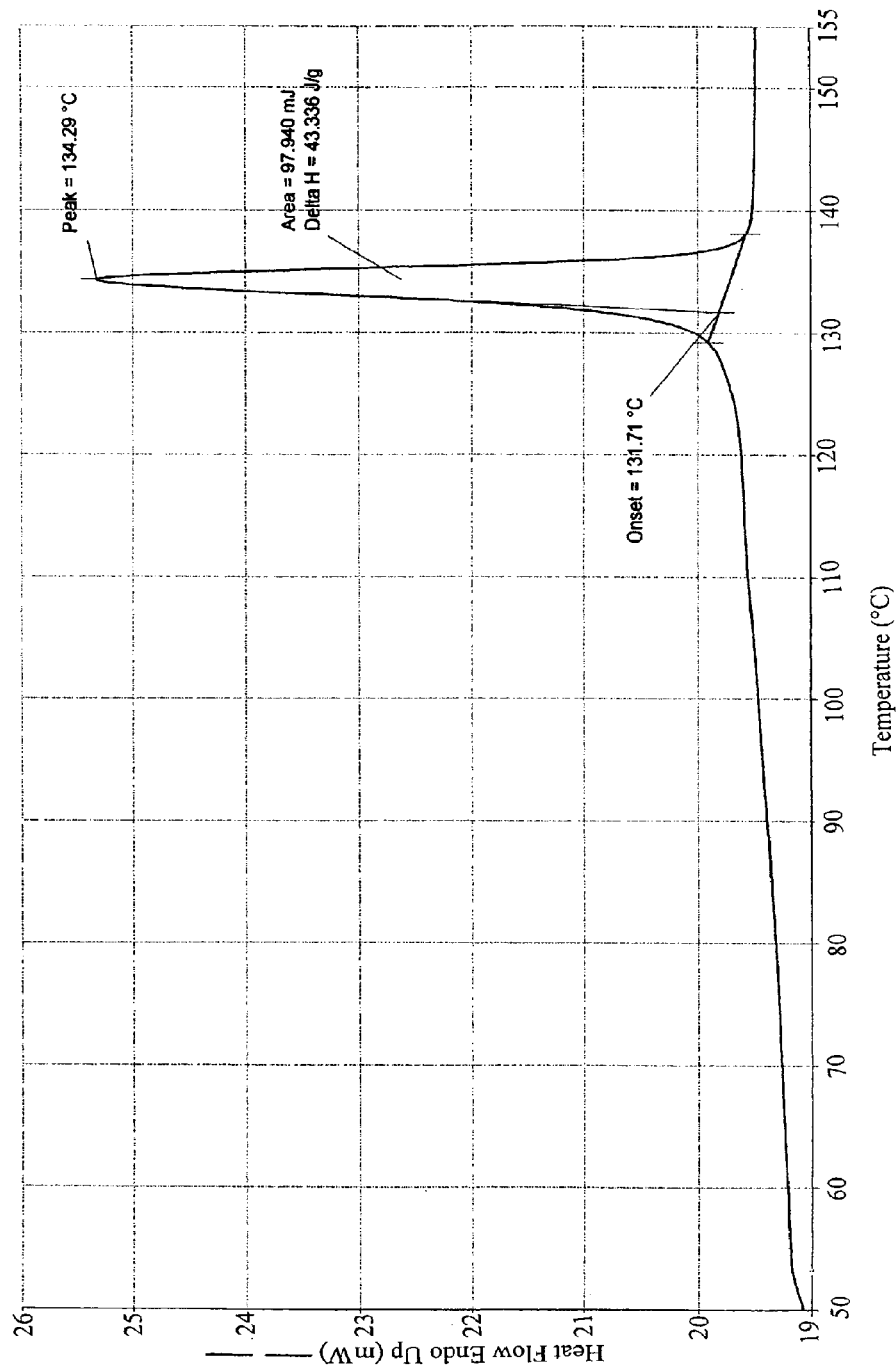
FIG. 14 shows a DSC spectrum of crystalline form III of cortexolone-17α-propionate.
Figure 15:
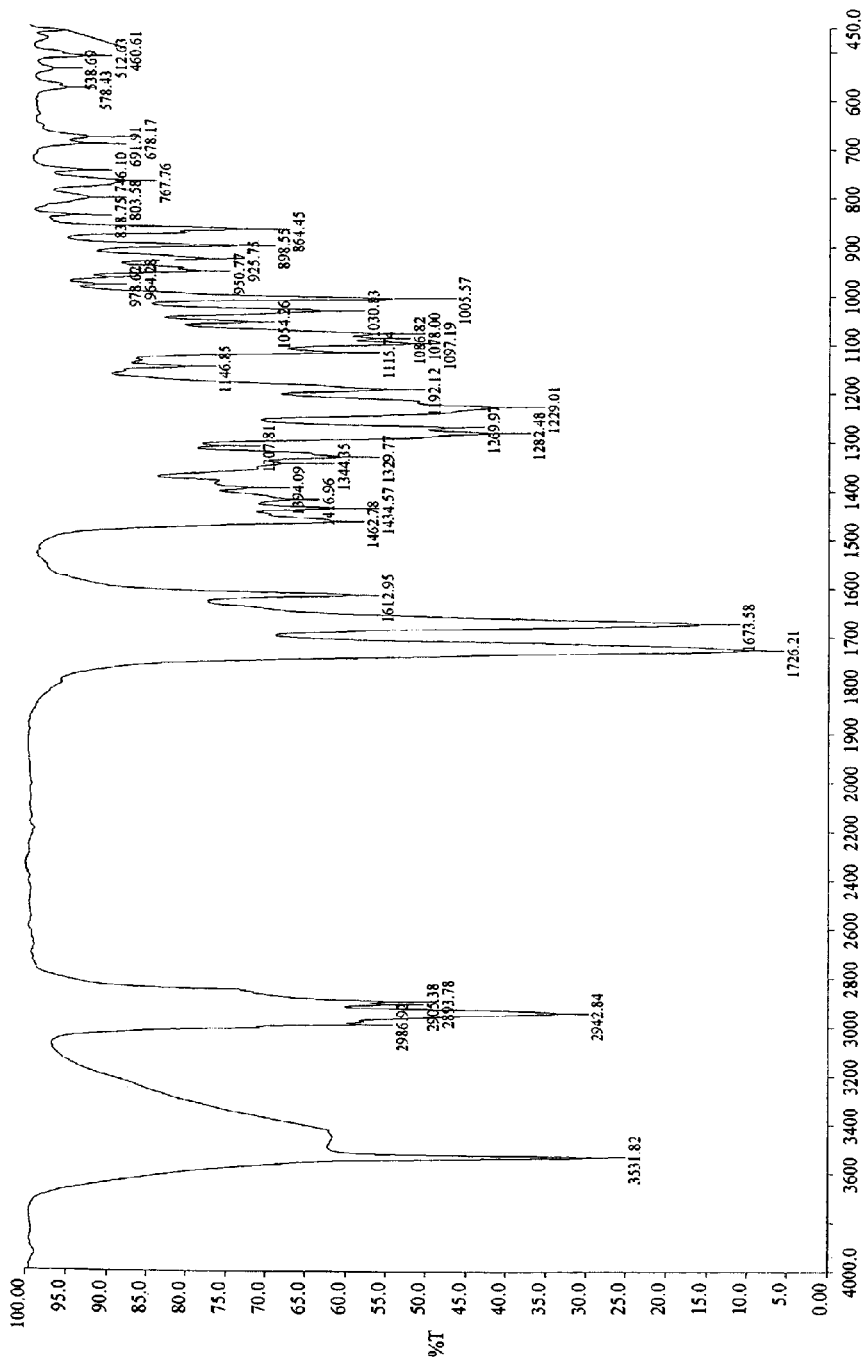
FIG. 15 shows an IR spectrum of crystalline form III of cortexolone-17α-propionate.

The crystalline form III obtained from ethanol/water has a DRX as shown in FIG. 13 and/or a DSC as shown in FIG. 14 and/or an IR as shown in FIG. 15.

The crystalline form I of 9,11-dehydro-17α-cortexolone is preferably obtained from tert-butylmethylether, diisopropylether, a dichloromethane/n-hexane mixture preferably in a ratio of 1/15, or an acetone/n-hexane mixture preferably in a ratio of 1/5.

Figure 16:
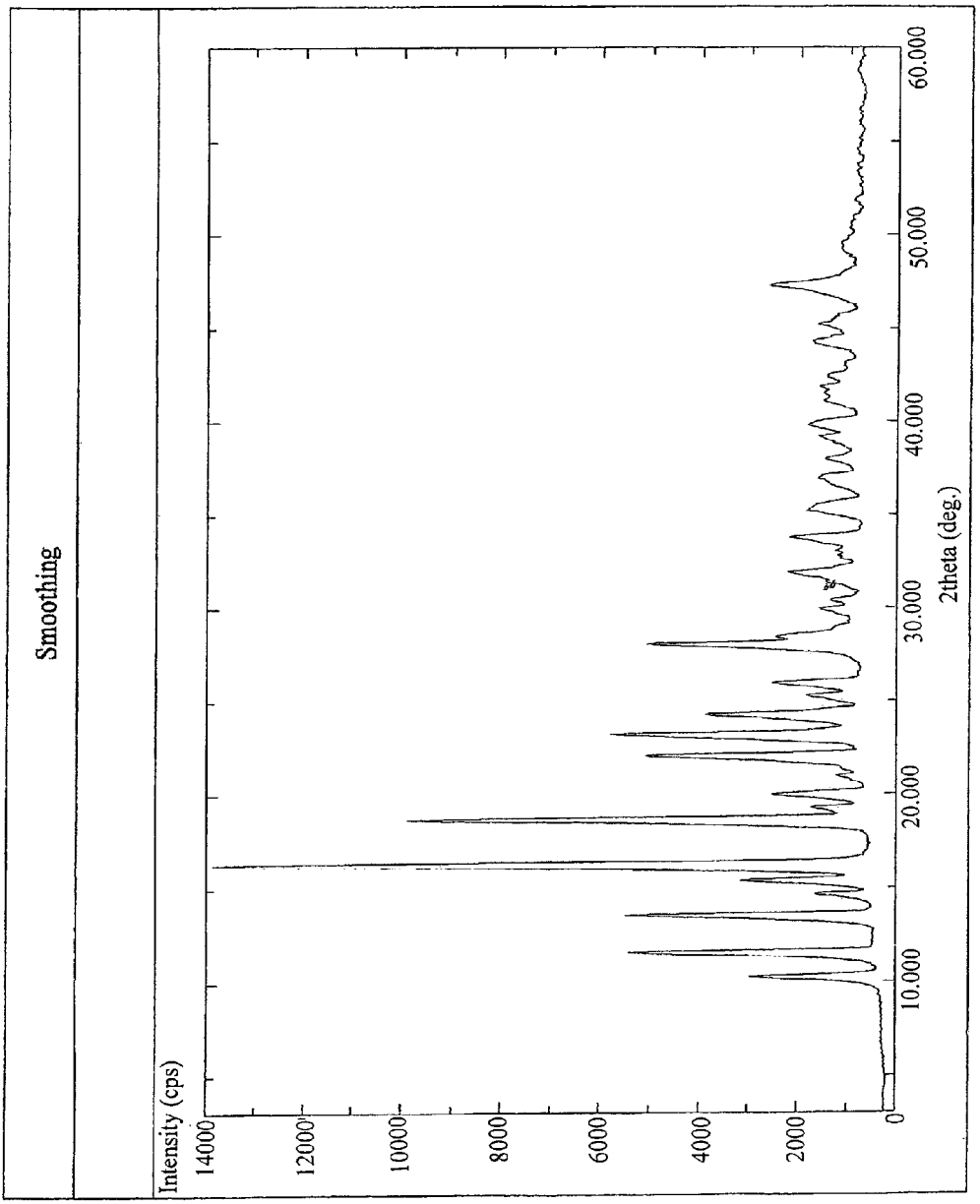
FIG. 16 shows a DRX spectrum of crystalline form I of cortexolone-17α-propionate.
Figure 17:
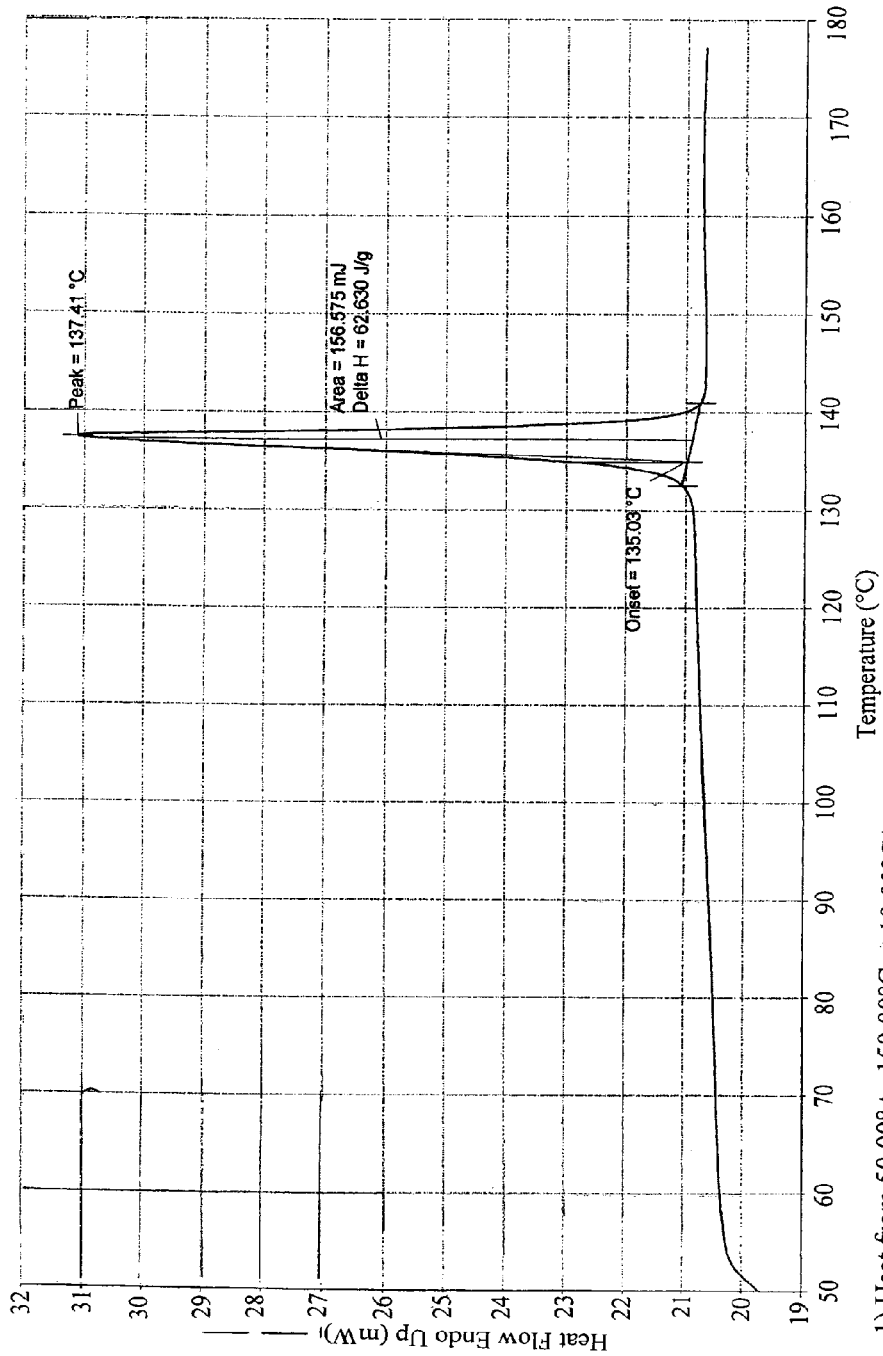
FIG. 17 shows a DSC spectrum of crystalline form I of cortexolone-17α-propionate.
Figure 18:
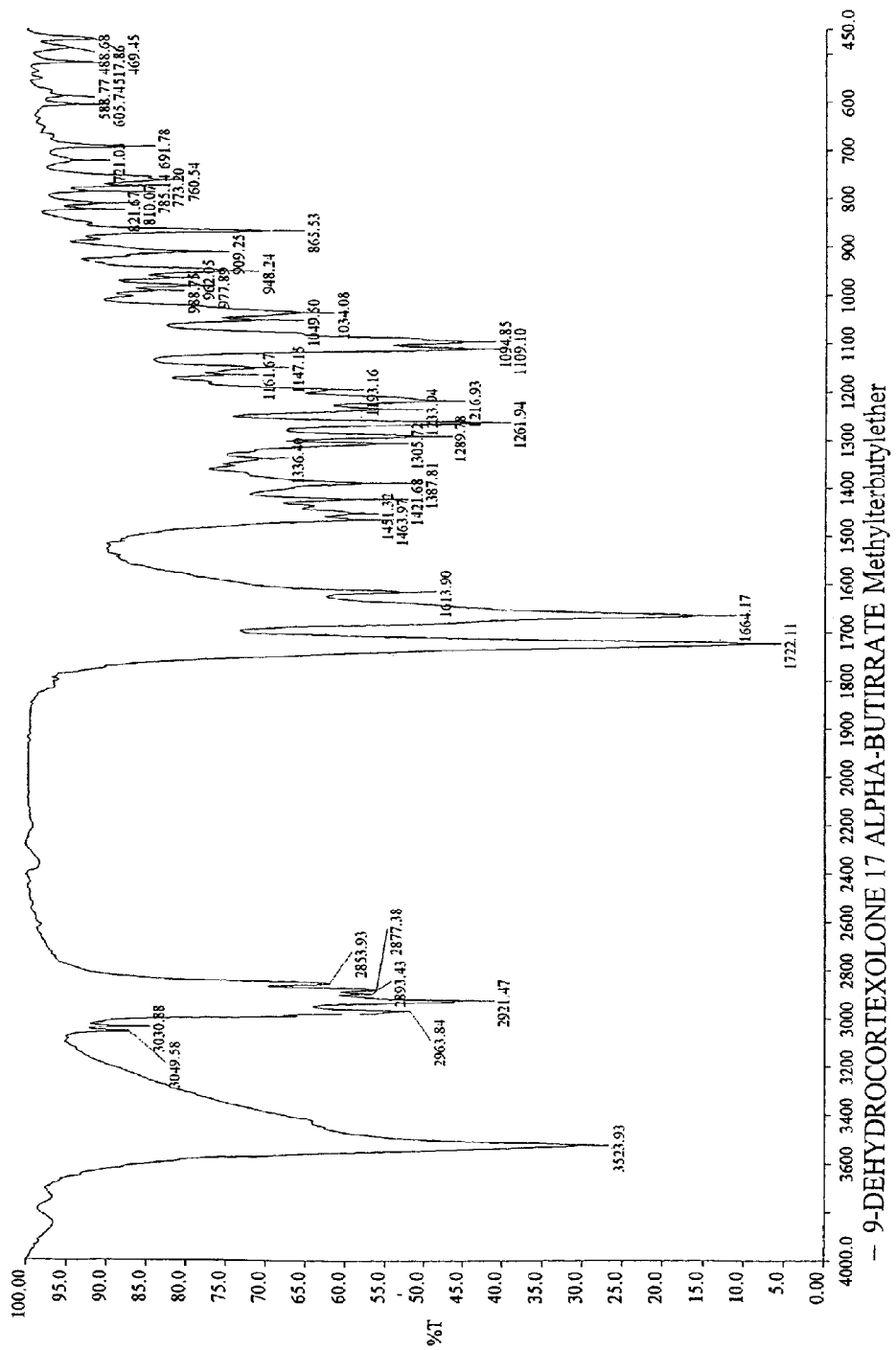
FIG. 18 shows an IR spectrum of crystalline form I of cortexolone-17α-propionate.

The crystalline form I obtained from tert-butylmethylether has a DRX as shown in FIG. 16 and/or a DSC as shown in FIG. 17 and/or an IR as shown in FIG. 18.

Figure 19:
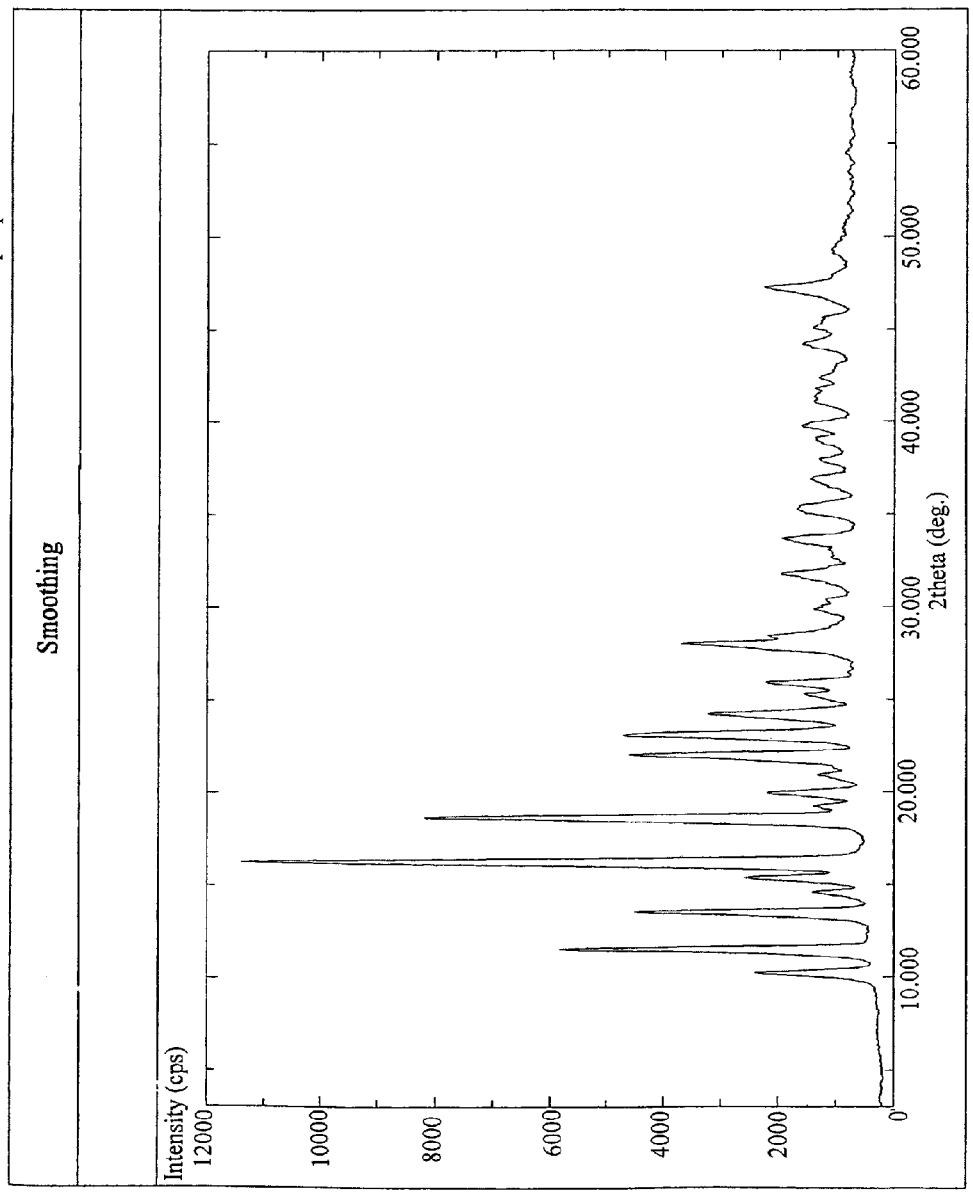
FIG. 19 shows a DRX spectrum of crystalline form I of cortexolone-17α-propionate.
Figure 20:
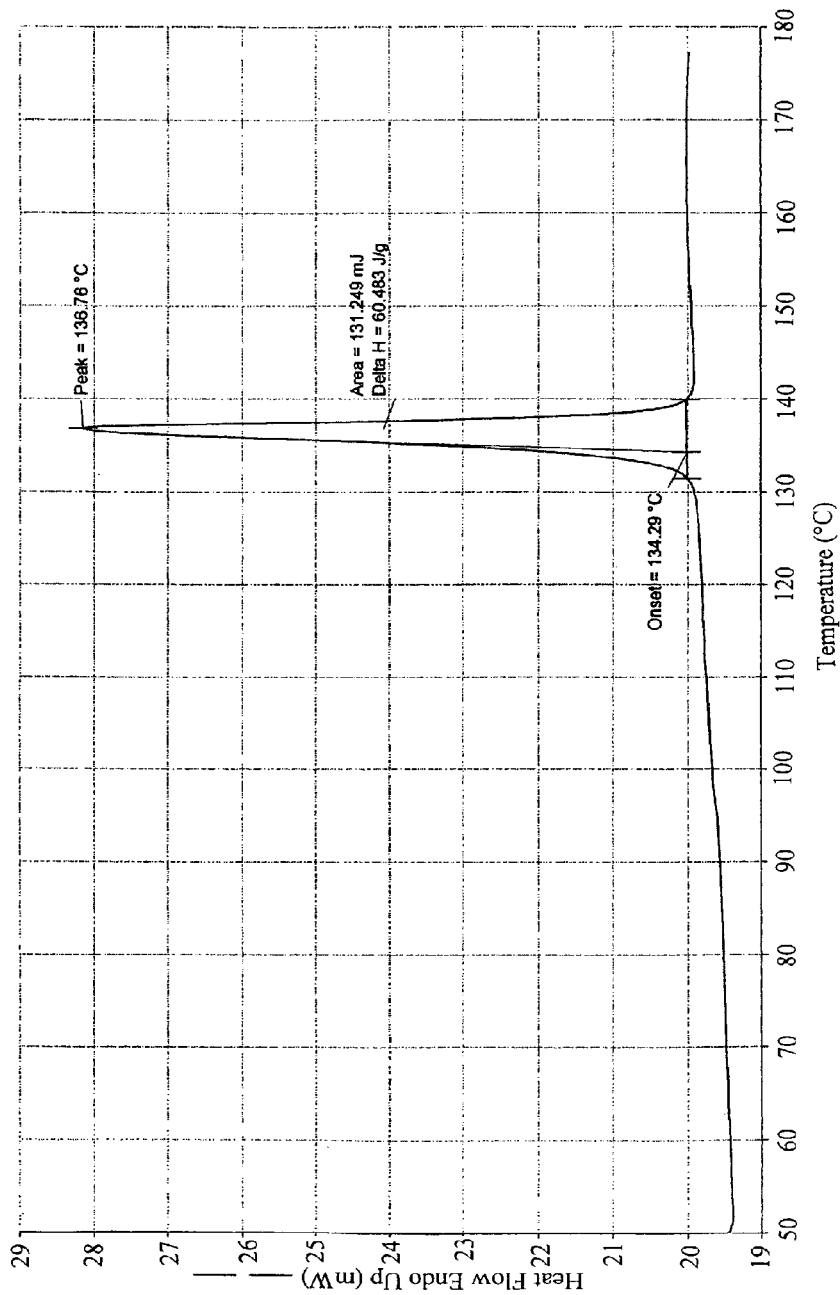
FIG. 20 shows a DSC spectrum of crystalline form I of cortexolone-17α-propionate.
Figure 21:
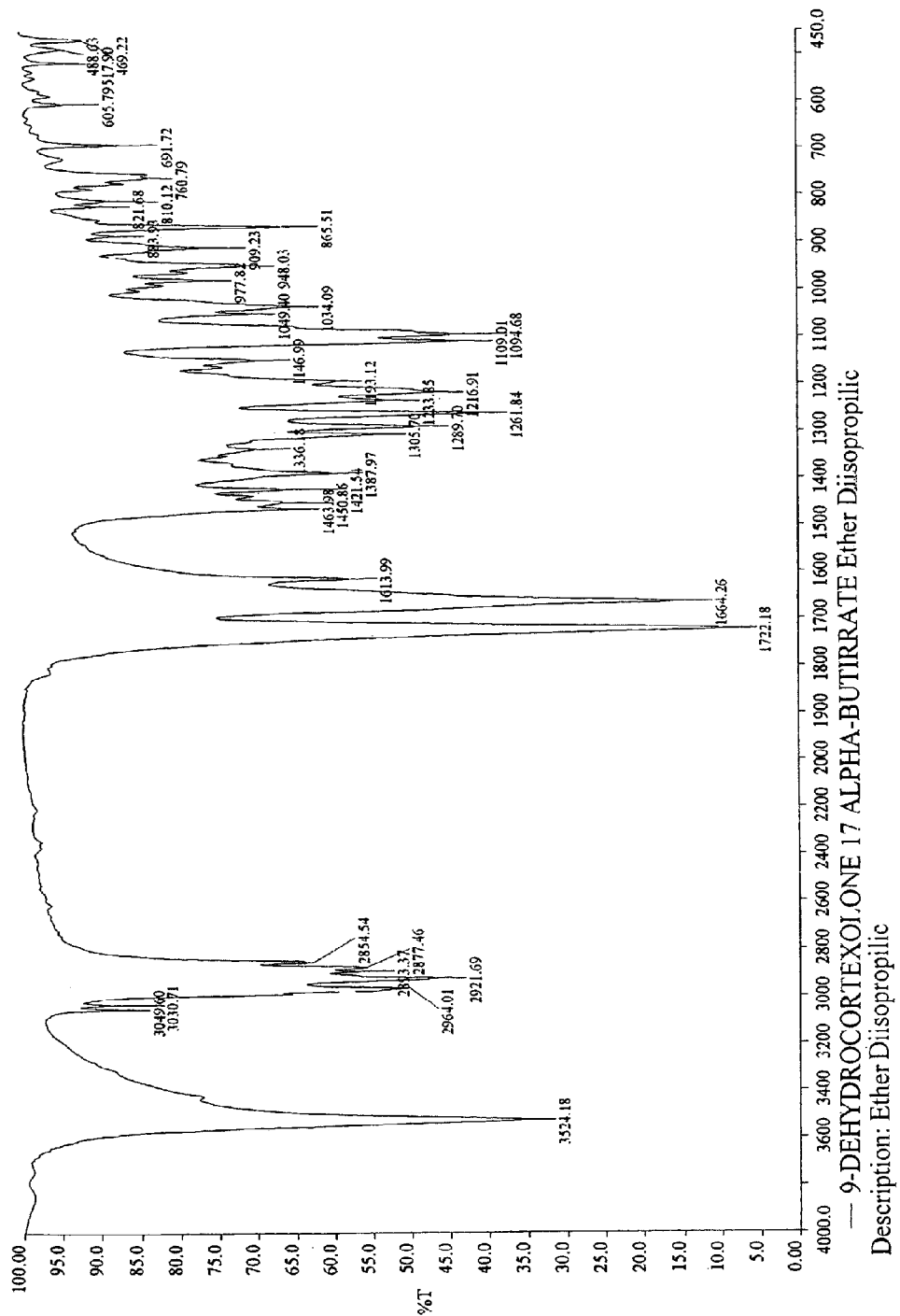
FIG. 21 shows an IR spectrum of crystalline form I of cortexolone-17α-propionate.

The crystalline form I obtained from diisopropylether has a DRX as shown in FIG. 19 and/or a DSC as shown in FIG. 20 and/or an IR as shown in FIG. 21.

Figure 22:
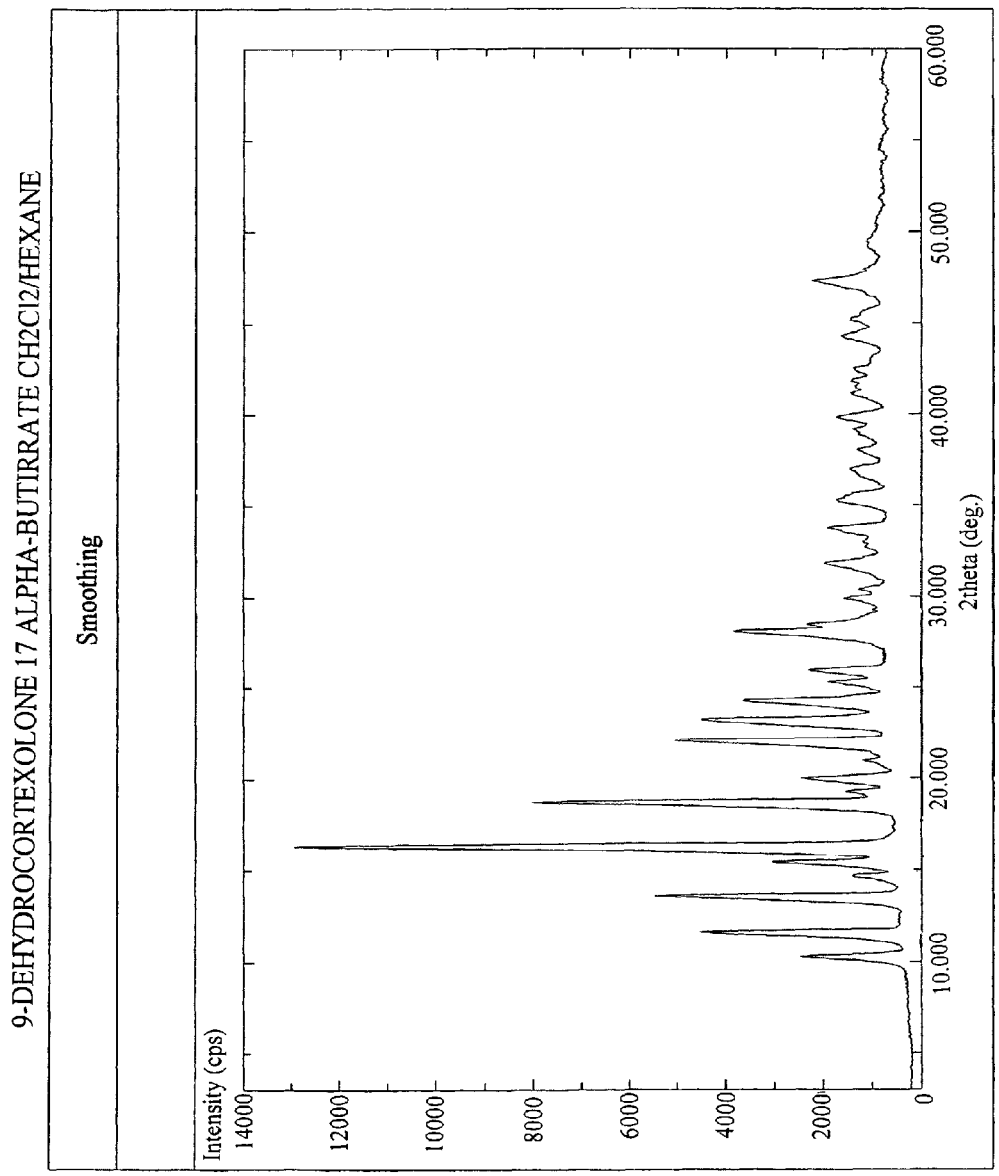
FIG. 22 shows a DRX spectrum of crystalline form I of cortexolone-17α-propionate.
Figure 23:
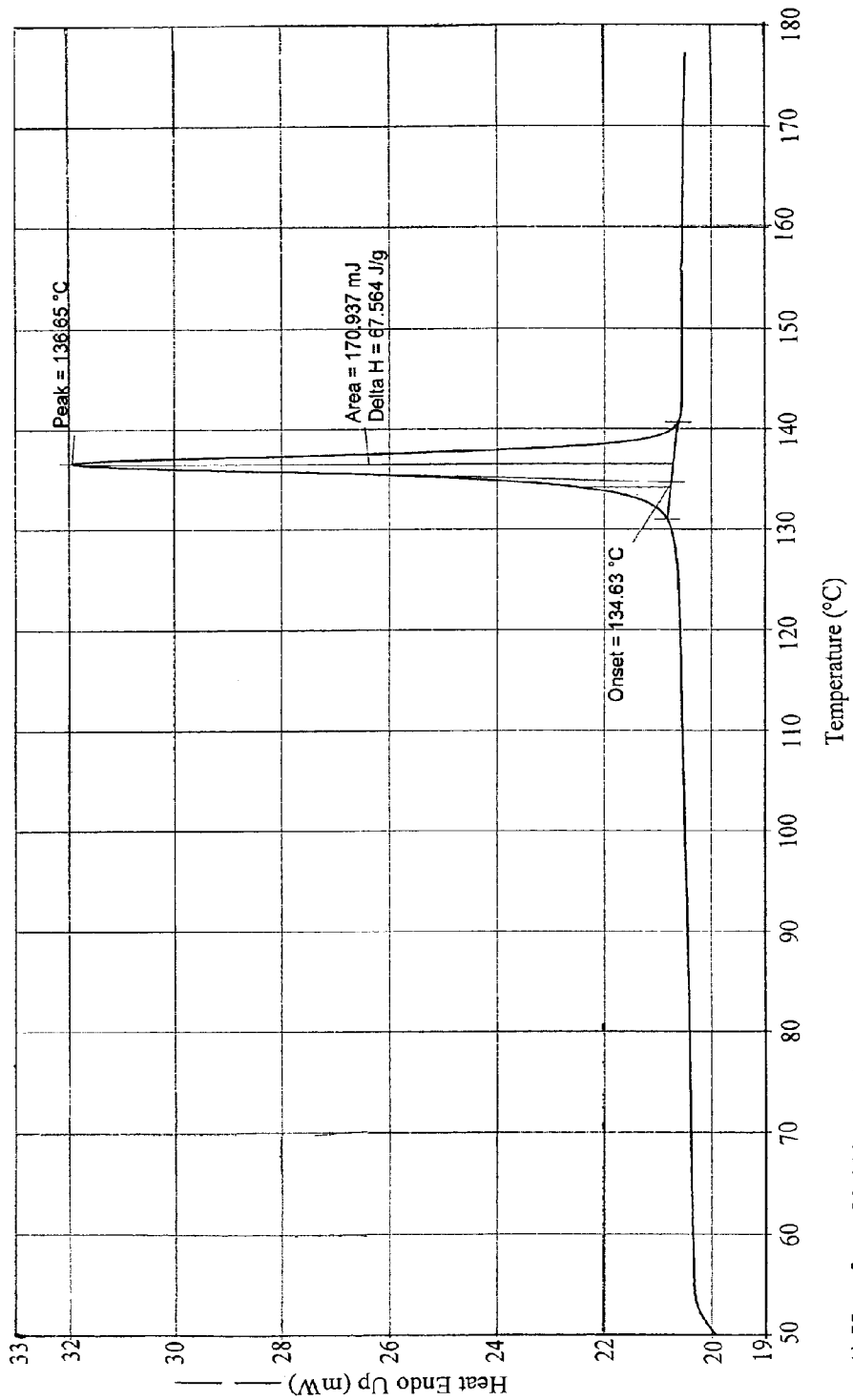
FIG. 23 shows a DSC spectrum of crystalline form I of cortexolone-17α-propionate.
Figure 24:
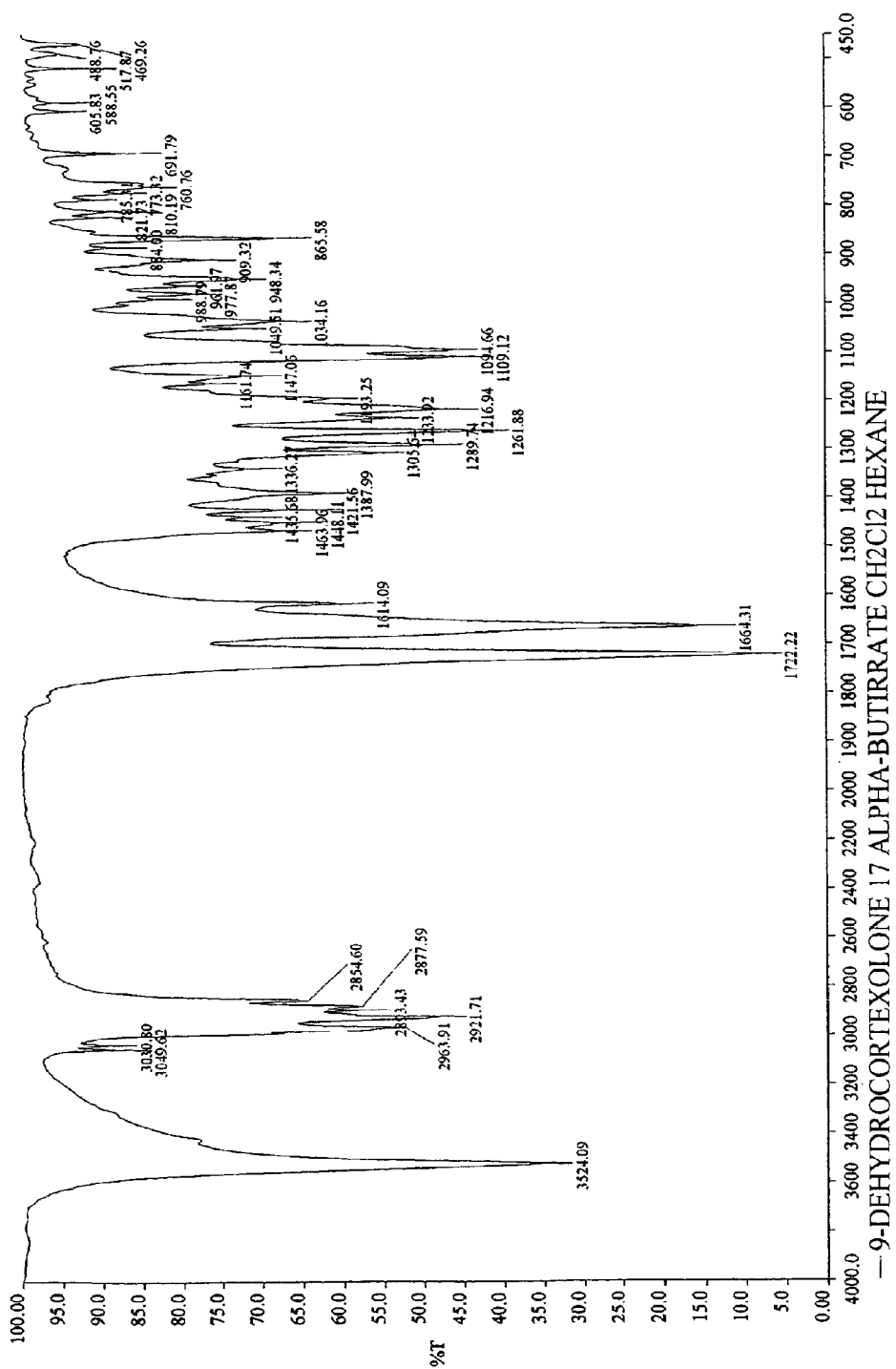
FIG. 24 shows an IR spectrum of crystalline form I of cortexolone-17α-propionate.

The crystalline form I obtained from dichloromethane/n-hexane has a DRX as shown in FIG. 22 and/or a DSC as shown in FIG. 23 and/or an IR as shown in FIG. 24.

Figure 25:
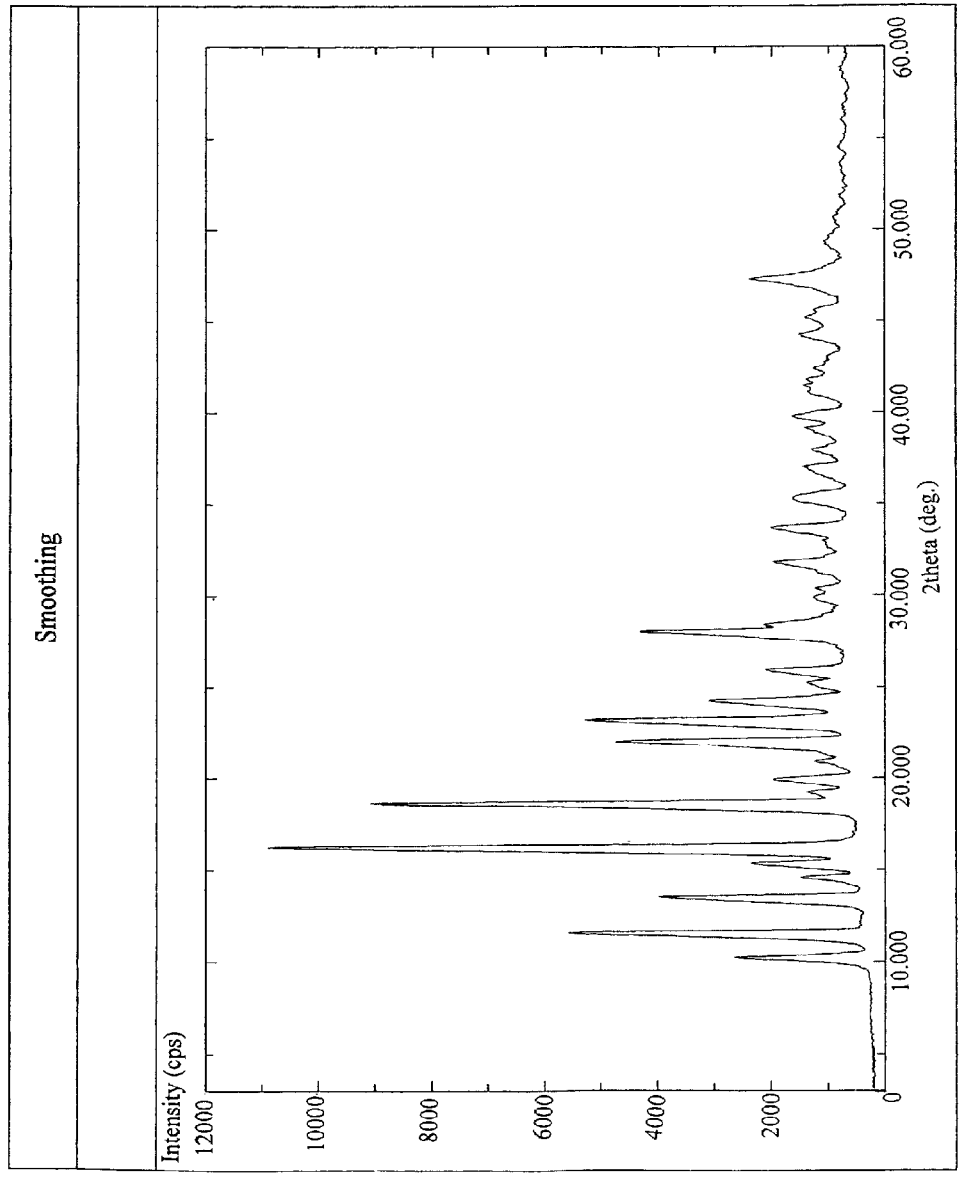
FIG. 25 shows a DRX spectrum of crystalline form I of cortexolone-17α-propionate.
Figure 26:
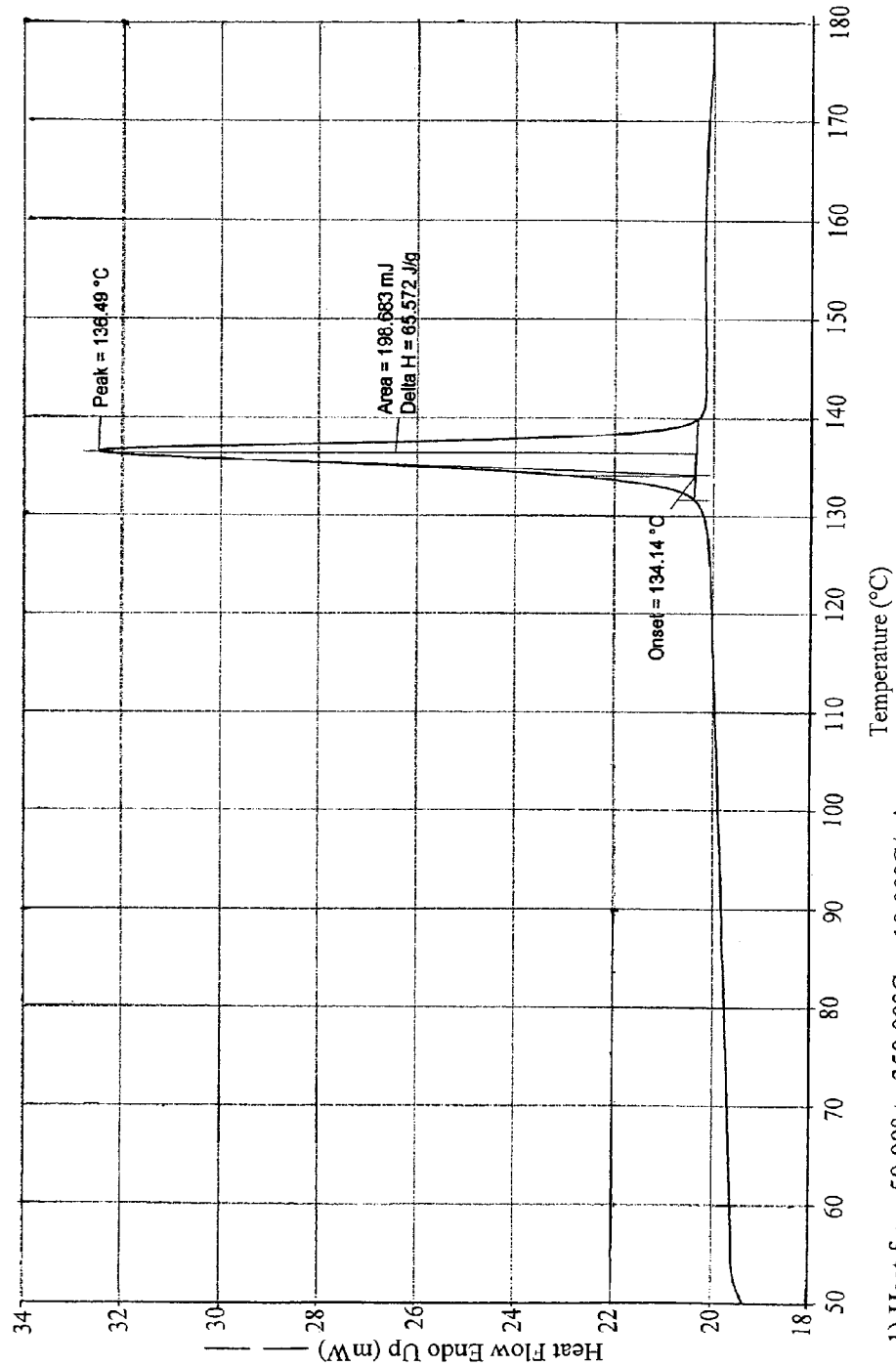
FIG. 26 shows a DSC spectrum of crystalline form I of cortexolone-17α-propionate.
Figure 27:
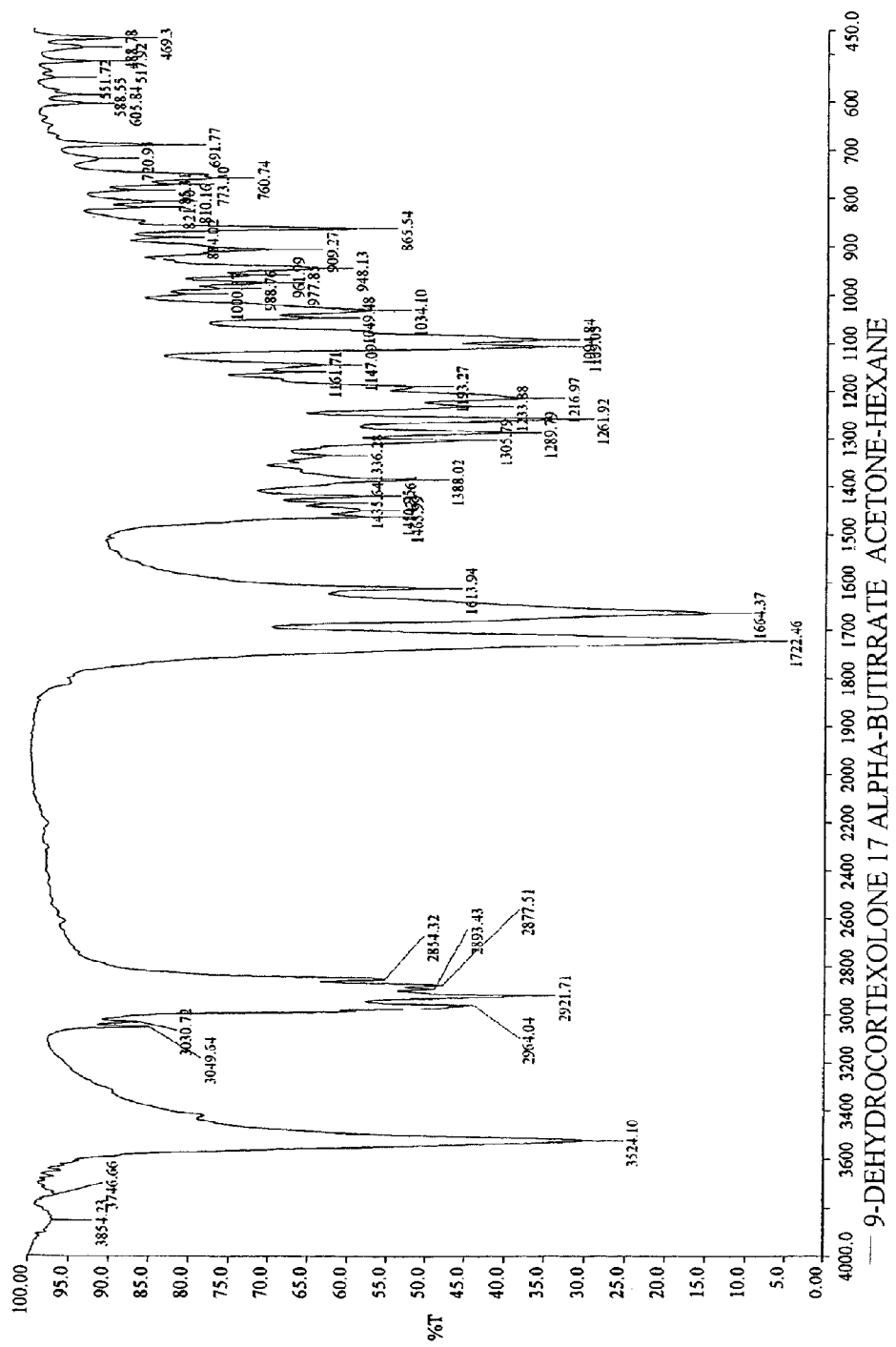
FIG. 27 shows an IR spectrum of crystalline form I of cortexolone-17α-propionate.

The crystalline form I obtained from acetone/n-hexane has a DRX as shown in FIG. 25 and/or a DSC as shown in FIG. 26 and/or an IR as shown in FIG. 27.

The differences observable in the DRX diagrams regarding the form III of 17α-propionate and regarding the form I of 9,11-dehydro derivative are to be deemed irrelevant in that they are due to the phenomena of crystal disorientation. Likewise, the differences observed in IR and DSC are to be deemed irrelevant in that they are due to variations when preparing the sample and/or when performing the analysis.

Table 3 shows some identification parameters and conditions for obtaining the abovementioned crystalline forms.

TABLE 3

| Compound of formula I (monoester) | Solid form | Solvents | Concentrations (g compound/ml solvent) | Melting point (° C.) | DRX | DSC | IR |
|---|---|---|---|---|---|---|---|
| Cortexolone 17α-propionate | Crystalline form I | Tert-butylmethylether | 1 g/10 ml | 133-135 | FIG. 1 | 134.90° C. (ΔH = 40.68 J/g) FIG. 2 | FIG. 3 |
| | Crystalline form II | diisopropylether | 1 g/60 ml | 114-116 | FIG. 4 | 115.85° C. (ΔH = 46.61 J/g) FIG. 5 | FIG. 6 |
| | Crystalline form III | dichloromethane/n-hexane | 1 g/15.51 ml (dichloromethane/n-hexane 1/30) | n.d. | FIG. 7 | 134.90° C. (ΔH = 42.45 J/g) FIG. 8 | FIG. 9 |
| | Crystalline form III | Acetone/n-hexane | 1 g/9 ml (acetone/n-hexane 1/8) | n.d. | FIG. 10 | 134.18° C. (ΔH = 43.83 J/g) FIG. 11 | FIG. 12 |

TABLE 3-continued

| Compound of formula I (monoester) | Solid form | Solvents | Concentrations (g compound/ml solvent) | Melting point (° C.) | DRX | DSC | IR |
|---|---|---|---|---|---|---|---|
| | Crystalline form III | Ethanol/water | 1 g/24 ml (ethanol/water 1/2) | n.d | FIG. 13 | 134.29° C. (ΔH = 43.34 J/g) FIG. 14 | FIG. 15 |
| 9,11-dehydro 17α-cortexolone | Crystalline form I | Tert-butylmethylether | 1 g/24 ml | n.d. | FIG. 16 | 137.45° C. (ΔH = 62.63 J/g) FIG. 17 | FIG. 18 |
| | Crystalline form I | diisopropylether | 1 g/96 ml | 136 | FIG. 19 | 136.76° C. (ΔH = 60.48 J/g) FIG. 20 | FIG. 21 |
| | Crystalline form I | Dichloromethane/ n-hexane | 1 g/16 ml (dichloromethane/ n-hexane 1/15) | n.d. | FIG. 22 | 136.65° C. (ΔH = 66.66 J/g) FIG. 23 | FIG. 24 |
| | Crystalline form I | Acetone/n-hexane | 1 g/21 ml (acetone/n-hexane 1/5) | n.d. | FIG. 25 | 136.49° C. (ΔH = 67.64 J/g) FIG. 26 | FIG. 27 |

The existence of a pseudo polymorph crystalline form of 17α-propionate, characterized by the presence of a crystallization water molecule and defined as solvate form IV was determined.

The solvate crystalline form IV of 17α-propionate is preferably obtained through crystallization from an organic/water solvent mixture in a ratio generally in the range of 1/2 to 2/1, preferably from propylene glycol/water in a ratio of 1/1 or polyethylenglycol/water in a ratio of 1/1.

The crystallization of 17α-propionate in solvate form may occur during the formulation processes of the final pharmaceutical form, where the manufacturing process of the pharmaceutical form provides for the dissolution of the active ingredient in an organic solvent, such as for example, propylene glycol, polyethylene glycol or short-chained aliphatic alcohols, followed by the addition of water in a ratio of 1/3 to 3/1 with respect to the organic solvents used for the dissolution of the active ingredient.

Furthermore, an object of the present invention is a pharmaceutical composition containing at least one of the crystalline forms described above in association with at least one physiologically acceptable excipient.

The compositions of the present invention can be of solid, semi-solid, pasty or liquid form and they are preferably selected from among tablets, capsules, powders, pellets, suspensions, emulsions, solutions, creams, gel, ointment, lotions or pastes both ready to use or to be reconstituted before use.

Lastly, object of the present invention is the use, preferably for human beings, of at least one of the crystalline forms and/or solvates described above for the preparation of a medication for treating pathologies affecting the urogenital system, the endocrine system, the skin and/or the cutaneous appendages.

In particular, an object of the present invention is the use of a liquid or semi-liquid formulation for topical administration, such as for example, cream, gel, ointment, emulsion or dispersion containing cortexolone-17α-propionate in the range of 0.1 to 2% by weight, preferably in the range of 0.2 to 1%, in a crystalline form selected from among solvate forms I, II, III or IV, preferably in solvate form IV, both in solution and crystalline dispersion states, the latter being possibly obtained also in an extemporaneous manner by precipitation of the crystalline active ingredient upon addition of water or aqueous solution to a solution containing the same active ingredient in an organic solvent or a mixture of organic solvents, for the preparation of a medication for treating pathologies affecting the urogenital system, the endocrine system, the skin and/or or skin appendages.

Additionally, an object of the present invention is the use of a liquid or solid formulation for oral or systemic administration, such as for example, a tablet, capsule, granule or powder containing 9,11-dehydro-cortexolone-17α-butanoate in the dosage in the range of 4 to 65% by weight, preferably in the range of 5 to 50%, with respect to the total formulation when said total formulation has a final weight of 200 mg or in the range of 1 to 25% by weight, preferably in the range of 2 to 20%, when the total formulation has a final weight of 500 mg in a crystalline form selected between solvate forms I, or IV, for treating pathologies affecting the urogenital system, the endocrine system, the skin and/or or skin appendages.

Said pathologies according to the invention are preferably selected from among acne, seborrhoeic dermatitis, androgenetic alopecia, hirsutism, benign prostatic hyperplasia, forms of prostate cancer, male contraception, polycystic ovary syndrome, control of aggressive or aberrant sexual behaviors and syndrome of precocious puberty.

The following examples are included to enhance the understanding of the present invention without restricting it in any way whatsoever.

EXAMPLES

Example 1

Alcoholysis with CCL of Cortexolone 17α,21-dipropionate

Add butanol (0.4 g, 5.45 mmoles) and CCL (17.4 g, 3.86 U/mg, FLUKA) to a solution of cortexolone-17α,21-dipropionate (0.5 g, 1.09 mmoles) in toluene (50 ml). Maintain the mixture under stirring, at 30° C., following the progress of the reaction in TLC (Toluene/ethyl acetate 6/4) until the initial material is dissolved (24 h). Remove the enzyme by means of filtration using a Celite layer. Recover the cortexolone 17α-propionate (0.437, 99%) after evaporation under low pressure. Through crystallization from diisopropyl ether you obtain a product with a purity >99% in HPLC.

$^1$H-NMR (500 MHz, CDCl$_3$) relevant signals δ (ppm) 5.78 (br s, 1H, H-4), 4.32 (dd, 1H, H-21), 4.25 (dd, 1H, H-21), 1.22 (s, 3H, CH$_3$-19), 1.17 (t, 3H, CH$_3$), 0.72 (s, 3H, CH$_3$-18). P.f. 114° C.

Example 2

According to the method described in example 1 prepare cortexolone-17α-butanoate.

IH-NMR relevant signals δ (ppm) 5.78 (br s, 1H, H-4), 4.32 (dd, 1H, H-21), 4.26 (dd, 1H, H-21), 1.23 (s, 3H, CH$_3$-19), 0.97 (t, 3H, CH$_3$), 0.73 (s, 3H, CH$_3$-18). P.F. 134-136° C.

Example 3

According to the method described in the example prepare cortexolone-17α-valerate.

$^1$H-NMR relevant signals δ (ppm) 5.77 (br s, 1H, H-4), 4.32 (dd, 1H, H-21), 4.26 (dd, 1H, H-21), 1.22 (s, 3H, CH$_3$-19), 0.95 (t, 3H, CH$_3$), 0.72 (s, 3H, CH$_3$-18). P.f 114° C. (diisopropyl ether).

Example 4

According to the method described in the example prepare 9,11-dehydro-cortexolone-17α-butanoate.

$^1$H-NMR relevant signals δ (ppm) 5.77 (br s, 1H, H-4), 5.54 (m, 1H, H-9), 4.29 (dd, 1H, H-21), 4.24 (dd, 1H, H-21), 1.32 (s, 3H, CH$_3$-19), 0.94 (t, 3H, CH$_3$), 0.68 (s, 3H, CH$_3$-18). P.f 135-136° C. (acetone/hexane).

Example 5

Alcoholysis with CALB of cortexolone-17α,21-dipropionate

Dissolve cortexolone, 17α, 2-dipropionate (0.5 g, 1.09 mmoles) in acetonitrile (40 ml), add CALB (2.3 g, 2.5 U/mg Fluka) and octanol (0.875 ml). Leave the mixture under stirring, at 30° C., for 76 hrs. Remove the enzyme by means of filtration using a paper filter. Once the solvents evaporate, recover a solid (0.4758) which upon analysis $^1$H-NMR shall appear made up of cortexolone-17α-propionate at 91%.

Example 6

Crystallization

Add the solvent (t-butylmethylether or diisopropylether) to the sample according to the ratios indicated in Table 3. Heat the mixture to the boiling temperature of the solvent, under stirring, until the sample dissolves completely. Cool to room temperature and leave it at this temperature, under stirring, for 6 hours. Filter using a buchner funnel and maintain the solid obtained, under low pressure, at a room temperature for 15 hours and then, at 40° C., for 5 hours.

Example 7

Precipitation

Dissolve the sample in the suitable solvent (dichloromethane, acetone, ethyl acetate or ethanol) according to the ratios indicated in table 3 and then add the solvent, hexane or water, according to the ratios indicated in table 3, maintaining the mixture, under stirring, at room temperature. Recover the precipitate by filtration using a buchner funnel and desiccate as in example 6.

Example 8

Obtaining a pharmaceutical form containing the medication in a defined crystalline form.

Prepare a fluid cream containing 2% cetylic alcohol, 16% glyceryl monostearate, 10% vaseline oil, 13% propylene glycol, 10% polyethylenglycol with low polymerization 1.5% polysorbate 80 and 47.5% purified water. Add 1 g of cortexolone 17α-propionate of crystalline form III to 100 g of this cream and subject the mixture to homogenization by means of a turbine agitator until you obtain homogeneity. You obtain a cream containing a fraction of an active ingredient dissolved in the formulation vehicle and a non-dissolved fraction of an active ingredient, present as a crystal of crystalline form III. This preparation is suitable for use as a formulation vehicle for skin penetration tests on Franz cells, where a coefficient of penetration in the range of 0.04 to 0.03 cm/h is observed on the preparation.

Example 9

Obtaining the Pharmaceutical Form Containing the Medication in Solvate Form IV for Replacing the Solvent During the Galenic Formulation Procedure Dissolve 100 g of cortexolone 17α-propionate of crystalline form III in 2500 g of propylene glycol under stirring at room temperature. Separately prepare, by using a turboemulsifier raising the temperature up to about 70° C., an emulsion with 250 g of Cetylic alcohol, 1500 g of glyceryl monostearate, 1000 g of liquid paraffin, 5 g of mixed tocopherols, 100 g of polysorbate 80 and 4650 g of water. After cooling the emulsion up to about 30° C., add—under stirring and under negative pressure—the cortexolone 17α-propionate solution in propylene glycol. Maintain the emulsioned cream under stifling until you obtain homogeneity, making sure the temperature remains low by means the circulation of a coolant.

Figure 28:
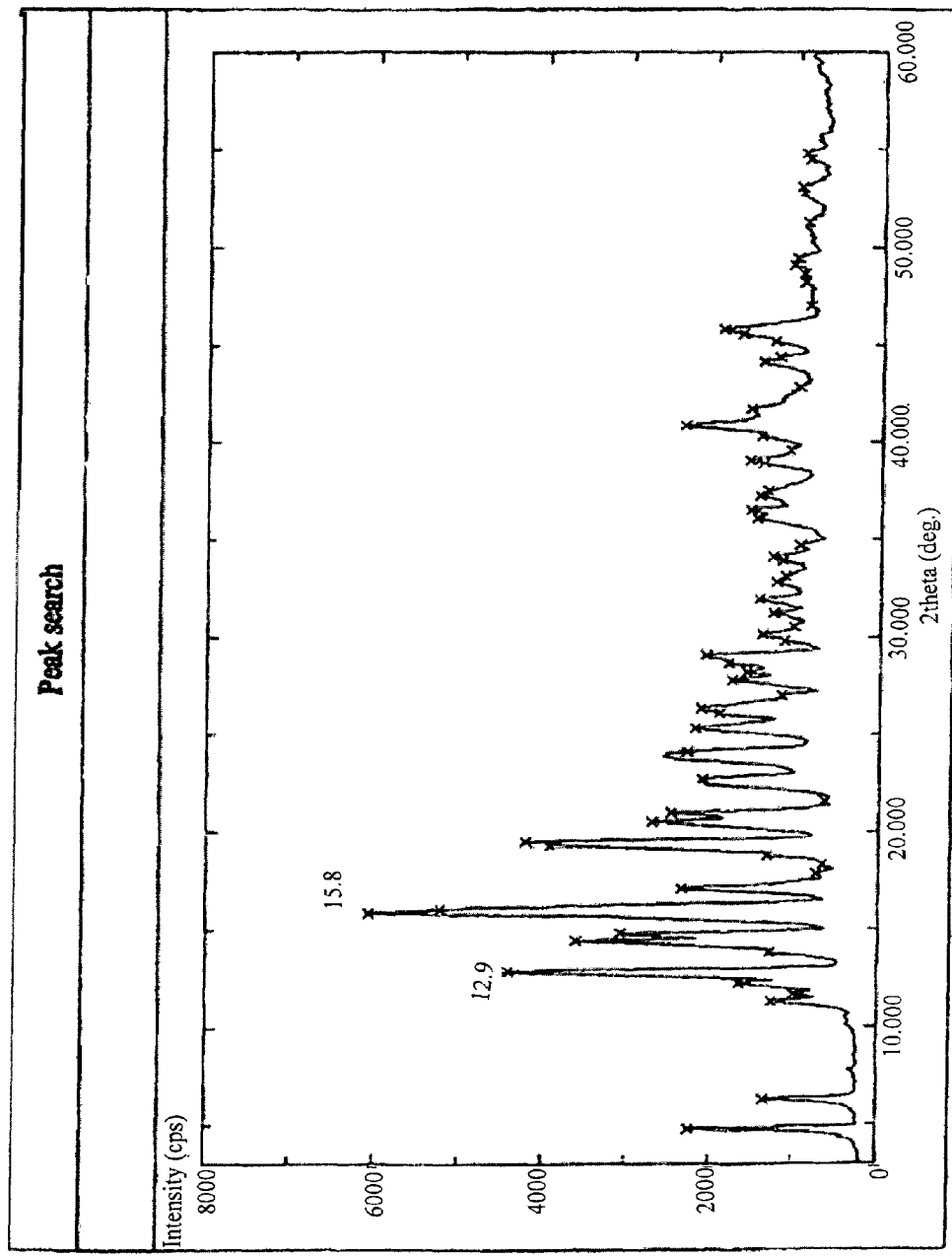
FIG. 28 shows a DRX spectrum of cortexolone-17α-propionate crystallized during the preparation of a cream formulation.

The cream contains a dispersed crystalline fraction, made up of an active ingredient in solvate crystalline form IV, formed due to the precipitation of the active ingredient itself from the glycolic solution which contained it when the latter was added to the predominantly aqueous formulation. The DRX spectra of the crystalline form present in the cream are indicated in FIG. 28.

What is claimed is:

1. Crystalline form IV of cortexolone-17α-propionate characterized by a DRX as shown in FIG. 28.

2. Crystalline form IV of cortexolone-17α-propionate characterized by XRPD peaks at about 4.8, 12.9, 14.4, 15.8, 16, 19.3, and 19.5 degrees 2theta.

3. A process for preparing crystalline form IV of cortexolone-17α-propionate, the process comprising crystallizing cortexolone-17α-propionate from a propylene glycol/water or polyethylene glycol/water mixture.

4. The process of claim 3, wherein the propylene glycol/water mixture has a ratio of propylene glycol to water of from about 1/2 to about 2/1.

5. The process of claim 4, wherein the ratio of propylene glycol to water is about 1/1.

6. The process of claim 3, wherein the polyethylene glycol/water mixture has a ratio of polyethylene glycol to water of from about 1/2 to about 2/1.

7. The process of claim 6, wherein the ratio of polyethylene glycol to water is about 1/1.

8. The process of claim 3, wherein the propylene glycol/water mixture has a ratio of propylene glycol to water of from about 1/3 to about 3/1.

9. Crystalline form IV of cortexolone-17α-propionate prepared by the process of claim 3.

10. Crystalline form IV of cortexolone-17α-propionate prepared by the process of claim 4.

11. Crystalline form IV of cortexolone-17α-propionate prepared by the process of claim 5.

12. Crystalline form IV of cortexolone-17α-propionate prepared by the process of claim 6.

13. Crystalline form IV of cortexolone-17α-propionate prepared by the process of claim 7.

14. A pharmaceutical composition comprising crystalline form IV of cortexolone-17α-propionate, water, and at least one physiologically acceptable excipient.

15. The composition of claim 14, wherein the at least one physiologically acceptable excipient is propylene glycol, cetylic alcohol, glyceryl monostearate, liquid paraffin, or a combination of any of the foregoing.

16. The composition of claim 14, further comprising mixed tocopherols, polysorbate 80, or a combination thereof.

17. The composition of claim 14, wherein the composition is in the form of a cream.

18. The composition of claim 14, wherein the composition further comprises solubilized cortexolone-17α-propionate.

19. The composition of claim 18, wherein the solubilized cortexolone-17α-propionate and crystalline form IV of cortexolone-17α-propionate together comprise 0.1 to 2% by weight of the composition.

20. The composition of claim 19, wherein the solubilized cortexolone-17α-propionate and crystalline form IV of cortexolone-17α-propionate together comprise 0.2 to 1% by weight of the composition.

21. The composition of claim 14, wherein the crystalline form IV of cortexolone-17α-propionate is present at from about 0.1 to about 2% by weight of the composition.

22. A pharmaceutical composition comprising crystalline form IV of cortexolone-17α-propionate.

23. The composition of claim 22, wherein the composition is in the form of a tablet, capsule, powder, pellet, suspension, emulsion, cream, gel, ointment, lotion, or paste.

24. The composition of claim 22, wherein the composition is in the form of a solid, semi-solid, or a paste.

* * * * *

UNITED STATES PATENT AND TRADEMARK OFFICE
CERTIFICATE OF CORRECTION

PATENT NO.      : 9,433,628 B2
APPLICATION NO. : 14/073928
DATED           : September 6, 2016
INVENTOR(S)     : Ajani et al.

Page 1 of 1

It is certified that error appears in the above-identified patent and that said Letters Patent is hereby corrected as shown below:

In the Claims

In Column 12, Line 54, Claim 2, delete "XRPD" and insert --DRX--.

Signed and Sealed this
Twelfth Day of June, 2018

Andrei Iancu
*Director of the United States Patent and Trademark Office*